United States Patent [19]

Takaya et al.

[11] 4,371,531
[45] Feb. 1, 1983

[54] CEPHALOSPORIN COMPOUNDS

[75] Inventors: Takao Takaya, Sakai; Takashi Masugi, Toyonaka; Takashi Ogino, Kobe; Kiyoshi Tsuji, Osaka, all of Japan

[73] Assignee: Fujisawa Pharmaceutical Company, Ltd., Osaka, Japan

[21] Appl. No.: 178,898

[22] Filed: Aug. 18, 1980

Related U.S. Application Data

[60] Division of Ser. No. 916,858, Jun. 19, 1978, Pat. No. 4,242,510, which is a continuation-in-part of Ser. No. 863,923, Dec. 23, 1977, abandoned.

[30] Foreign Application Priority Data

Dec. 27, 1976 [JP] Japan .................. 51-160698
Dec. 5, 1977 [JP] Japan .................. 52-146327

[51] Int. Cl.³ .................................. A61K 31/545
[52] U.S. Cl. ...................... 424/246; 544/22; 544/28
[58] Field of Search ............... 544/22, 28; 424/246

[56] References Cited

U.S. PATENT DOCUMENTS

| | | | |
|---|---|---|---|
| 3,966,717 | 6/1976 | Cook et al. | 544/22 |
| 4,007,176 | 2/1977 | Berger et al. | 544/28 |
| 4,034,090 | 7/1977 | Berger et al. | 544/22 |
| 4,071,531 | 1/1978 | Berger et al. | 544/28 |
| 4,091,209 | 5/1978 | Cook et al. | 424/246 |
| 4,098,888 | 7/1978 | Ochiai et al. | 544/28 |

*Primary Examiner*—Paul M. Coughlan, Jr.
*Attorney, Agent, or Firm*—Oblon, Fisher, Spivak, McClelland & Maier

[57] ABSTRACT

The invention relates to new cephalosporin compounds of high antimicrobial activity, the compounds being of the formula:

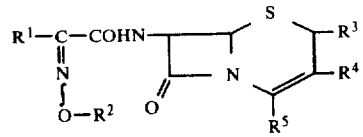

wherein $R^1$ is a group of the formula

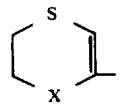

in which X is sulfur, oxygen, imino or lower-alkanoyl-substituted imino,
$R^2$ is hydrogen, lower alkyl or lower alkenyl,
$R^3$ is hydrogen or lower alkyl,
$R^4$ is hydrogen, halogen, lower alkyl, carbamoyloxymethyl or lower alkanoyloxymethyl, and
$R^5$ is carboxy or its ester, and a non-toxic, pharmaceutically acceptable salt thereof.

30 Claims, No Drawings

CEPHALOSPORIN COMPOUNDS

This is a division, of application Ser. No. 916,858, filed June 19, 1978, now U.S. Pat. No. 4,242,510, which is a continuation in part of abandoned application Ser. No. 863,923 filed Dec. 23, 1977, abandoned.

The present invention relates to new cephalosporin compounds and pharmaceutically acceptable salts thereof. More particularly, it relates to new cephalosporin compounds and pharmaceutically acceptable salts thereof which have antibacterial activities, to processes for the preparation thereof, to pharmaceutical composition comprising the same, and to a method of using the same therapeutically in the treatment of infectious diseases in human being and animals.

Accordingly, it is one object of the present invention to provide cephalosporin compounds and pharmaceutically acceptable salts thereof, which are highly active against a number of pathogenic bacteria.

Another object of the present invention is to provide processes for the preparation of cephalosporin compounds and pharmaceutically acceptable salts thereof.

A further object of the present invention is to provide pharmaceutical composition comprising, as an active ingredient, said cephalosporin compounds or pharmaceutically acceptable salt thereof.

Still further object of the present invention is to provide a method for the treatment of infectious diseases caused by pathogenic bacteria in human beings and animals.

The objective cephalosporin compounds of the present invention can be represented by the following formula (I):

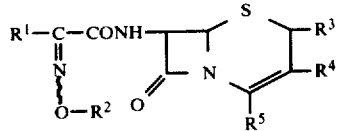

herein $R^1$ is a group of the formula:

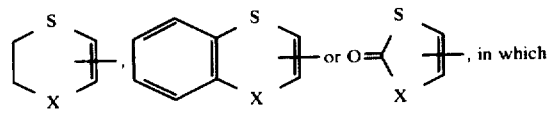

X is sulfur, oxygen or substituted or unsubstituted imino, $R^2$ is hydrogen, or a saturated or unsaturated aliphatic hydrocarbon residue, $R^3$ is hydrogen or lower alkyl, $R^4$ is hydrogen, halogen, lower alkyl, acyloxymethyl or heterocyclic-thiomethyl which may be substituted with lower alkyl, and $R^5$ is carboxy or its derivative, and nontoxic, pharmaceutically acceptable salts thereof.

In the formulae of the object compounds (I), and the corresponding starting compounds (III), the partial structure of the formula:

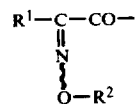

is to be understood to include the syn and anti isomers, of which structures are represented by the formulae:

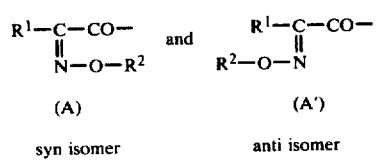

| (A) | (A') |
|---|---|
| syn isomer | anti isomer |

In this specifications, with regard to all the compounds having the above mentioned partial structure, the compounds having the geometrical structure shown by the formula (A) are referred to as "syn isomer" and the compounds having the alternative one shown by the formula (A') as "anti isomer".

In the above and subsequent descriptions of the present specifications, suitable examples and illustration of the various definitions which the present invention intends to include within the scope thereof are explained in details as follows.

The term "lower" is intended to mean 1 to 6 carbon atoms, unless otherwise provided.

"Saturated or unsaturated aliphatic hydrocarbon residue" for $R^2$ may include lower alkyl, lower alkenyl and lower alkynyl, and more particularly may include straight or branched lower alkyl such as methyl, ethyl, propyl, isopropyl, butyl, isobutyl, t-butyl, pentyl, neopentyl, hexyl and the like, preferably the one having 1 to 4 carbon atoms;

straight or branched lower alkenyl such as vinyl, allyl, 1-propenyl, 1-butenyl, 2-butenyl, 2-methyl-2-propenyl, 2-pentenyl, 3-pentenyl, 4-pentenyl, 2-hexenyl, 3-hexenyl, 1-hexenyl, 5-hexenyl and the like, preferably the one having 2 to 4 carbon atoms; and straight or branched lower alkynyl such as ethynyl, 1-propynyl, propargyl, 1-butynyl, 2-butynyl, 3-butynyl, 2-pentynyl, 3-pentynyl, 4-pentenyl, 2-hexenyl, 3-hexenyl, 4-hexenyl, 5-hexenyl and the like, preferably the one having 2 to 4 carbon atoms.

"Lower alkyl" for $R^3$ and $R^4$ may include straight or branched alkyl as illustrated hereinabove, preferably the one having 1 to 4 carbon atoms and most preferably methyl.

"Halogen" for $R^4$ may be chlorine, bromine, iodine and fluorine.

"Acyl" moiety of "acyloxymethyl" for $R^4$ may include lower alkanoyl and substituted or unsubstituted carbamoyl, particularly, suitable lower alkanoyl may be formyl, acetyl, propionyl, butyryl, isobutyryl, isovaleryl, oxalyl, succinyl, pivaloyl, and the like, and suitable substituted or unsubstituted carbamoyl may include carbamoyl, N-loweralkylcarbamoyl (e.g., N-methylcarbamoyl, N-ethylcarbamoyl, etc.), N-arylcarbamoyl (e.g., N-phenylcarbamoyl, etc.), N-(substituted or unsubstituted lower alkanoyl)carbamoyl (e.g., N-acetylcarbamoyl, N-trichloroacetylcarbamoyl, etc.), and the like. And, more preferred examples of the "acyloxymethyl" are carbamoyloxymethyl, acetyloxymethyl and the like.

"Substituted imino" for X in the definition of "$R^1$" means an imino group substituted by a substituent which is removable, and said substituent may include an acyl group and the other conventional protective group. And, the said acyl group may include aliphatic acyl, acyl having an aromatic ring, and the like.

Suitable aliphatic acyl may be lower alkanoyl (e.g. formyl, acetyl, propionyl, butyryl, isobutyryl, isovaleryl, oxalyl, succinyl, pivaloyl, etc.); lower alkoxycarbonyl (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.); and lower alkoxyalkanoyl (e.g., methoxyacetyl, ethoxyacetyl, methoxypropionyl, etc.), more preferably alkanoyl having 1 to 4 carbon atoms.

Suitable examples of the acyl having an aromatic ring may be ar(lower)alkanoyl (e.g., phenylacetyl, phenylpropionyl, etc.); ar(lower)alkoxycarbonyl (e.g., benzyloxycarbonyl, phenethyloxycarbonyl, etc.); and aroyl (e.g., benzoyl, toluoyl, naphthoyl, phthaloyl, indancarbonyl, etc.).

The acyl moiety as stated above (especially, the alkane moiety and the aromatic ring in the acyl) may have at least one suitable substituent such as halogen (e.g., chlorine, bromine, iodine or fluorine), hydroxy, cyano, nitro, lower alkoxy, haloalkyl (e.g. trifluoromethyl, etc.) and the like.

Suitable examples of the acyl having said substituent(s) may be:

substituted alkanoyl such as mono(or di or tri)halo(lower)alkanoyl (e.g. trifluoroacetyl, trichloroacetyl, etc.), mono(or di or tri)halo(lower)alkanoylcarbamoyl (e.g., trichloroacetylcarbamoyl, etc.), substituted ar(lower)alkanoyl (e.g., 4-chlorophenylacetyl, 3-chloro-4-hydroxyphenylacetyl, 4-nitrophenylacetyl, 4-methoxyphenylacetyl, 4-fluorophenylacetyl, 4-trifluoromethylphenylacetyl, etc.);

halo(lower)alkoxycarbonyl (e.g., chloroethoxycarbonyl, trichloroethoxycarbonyl, etc.); substituted ar(lower)alkoxycarbonyl such as haloar(lower)alkoxycarbonyl (e.g., 4-chlorobenzyloxycarbonyl, 3,4-dichlorobenzyloxycarbonyl, 4-trifluoromethylbenzyloxycarbonyl, etc.);

lower alkoxyar(lower)alkoxycarbonyl(e.g., 4-methoxybenzyloxycarbonyl, 3,4-dimethoxybenzyloxycarbonyl, 3,4,5-trimethoxybenzyloxycarbonyl, etc.);

substituted aroyl such as haloaroyl (e.g., 4-chlorobenzoyl, 3,4-dichlorobenzoyl, 3-trifluoromethylbenzoyl, 4-bromobenzoyl, etc.); lower alkoxyaroyl (e.g., 4-methoxybenzoyl, 3,4,5-trimethoxybenzoyl, etc.); 4-nitrobenzoyl, 4-methoxy-3-nitrobenzoyl, salicyloyl, 4-hydroxy-3-chlorobenzoyl, 5-hydroxy-2-naphthoyl,; and the like.

"Heterocycle" moiety of the "heterocyclic-thiomethyl which may be substituted with lower alkyl" for $R^4$ may include saturated or unsaturated, monocyclic or fused heterocyclic group, and preferable heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl, its N-oxide, pyrimidinyl, pyrazinyl, pyridazinyl, triazolyl, (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 6-membered heteromonocyclic group containing 1 to 4 nitrogen atoms (e.g., pyrrolidinyl, imidazolidinyl, piperidino, piperazinyl, etc.);

unsaturated condensed heterocyclic group containing 1 to 4 nitrogen atoms (e.g., indolyl, isoindolyl, indolizinyl, benzimidazolyl, quinolyl, isoquinolyl, indazolyl, benzotriazolyl, etc.);

unsaturated 3- to 6-membered heteromonocyclic group containing 1 to 2 oxygen atoms and 1 to 3 nitrogen atoms, for example, oxazolyl, isoxazolyl, oxadiazolyl, (e.g., 1,2,4-oxadiazolyl, 1,3,4-oxadiazolyl, 1,2,5-oxadiazolyl, etc.), etc.;

saturated 3- to 6-membered heteromonocyclic group containing 1 to 2 oxygen atoms and 1 to 3 nitrogen atoms (e.g., morpholinyl, etc.);

unsaturated fused heterocyclic group containing 1 to 2 oxygen atoms and 1 to 3 nitrogen atoms (e.g., benzoxazolyl, benzoxadiazolyl, etc.);

unsaturated 3 to 6-membered heteromonocyclic group containing 1 to 2 sulfur atoms and 1 to 3 nitrogen atoms, for example, thiazolyl, thiadiazolyl, (e.g., 1,2,4-thiadiazolyl, 1,3,4-thiadiazolyl, 1,2,5-thiadiazolyl, etc.), etc.;

saturated 3- to 6-membered heteromonocyclic group containing 1 to 2 sulfur atoms and 1 to 3 nitrogen atoms (e.g., thiazolidinyl, etc.);

unsaturated fused heterocyclic group containing 1 to 2 sulfur atoms and 1 to 3 nitrogen atoms (e.g., benzothiazolyl, benzothiadiazolyl, etc.) and the like, and said heterocyclic group may be substituted with lower alkyl such as methyl, ethyl, propyl, isopropyl, butyl, isobutyl, pentyl, cyclopentyl, hexyl, cyclohexyl, etc.

"Its derivative" for $R^5$ means "derivative at the carboxy group", and may include esterified carboxy in which said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);

lower alkenyl ester (e.g., vinyl ester, allyl ester, etc.); lower alkyl ester (e.g., ethynyl ester, propynyl ester, etc.); lower alkoxyalkyl ester (e.g., methoxymethyl ester, ethoxymethyl ester, isopropoxymethyl ester, 1-methoxyethyl ester, 1-ethoxyethyl ester, etc.); lower alkylthioalkyl ester (e.g., methylthiomethyl ester, ethylthiomethyl ester, ethylthioethyl ester, isopropylthiomethyl ester, etc.);

mono(or di or tri)-halo(lower)alkyl ester (e.g., 2-iodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g., mesylmethyl ester, 2-mesylethyl ester etc.);

ar(lower)alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-di-t-butylbenzyl ester, etc.);

aryl ester which may have one or more suitable substituent(s) (e.g., phenyl ester, tolyl ester, t-butylphenyl ester, xylyl ester, mesityl ester, cumenyl ester, etc.); tri(lower)alkyl silyl ester and the like.

Suitable pharmaceutically acceptable salts of the object compound (I) are conventional non-toxic salts and may include an inorganic salt, for example, a metal salt such as an alkali metal salt (e.g., sodium salt, potassium salt, etc.) and an alkaline earth metal salt (e.g., calcium salt, magnesium salt, etc.), ammonium salt, etc.; an organic salt, for example, an organic amine salt (e.g., trimethylamine salt, triethylamine salt, pyridine salt, picoline salt, dicyclohexylamine salt, N,N'-dibenzylethylenediamine salt, N-methylglucamine salt, diethanolamine salt, triethanolamine salt, tris(hydroxymethylamino)methane salt, etc:) etc.; an amino acid salt (e.g., arginine salt, lysine salt, etc.), and the like, among which the preferred pharmaceutically acceptable salt is an alkali metal salt and an alkaline earth metal salt.

According to the present invention, the object compounds (I) and the pharmaceutically acceptable salts thereof can be prepared by the processes as illustrated in the following scheme.

Process 1.

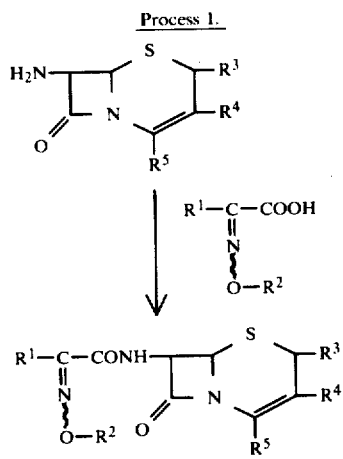

wherein $R^1$, $R^2$, $R^3$, $R^4$ and $R^5$ are each as defined above.

Process 2.

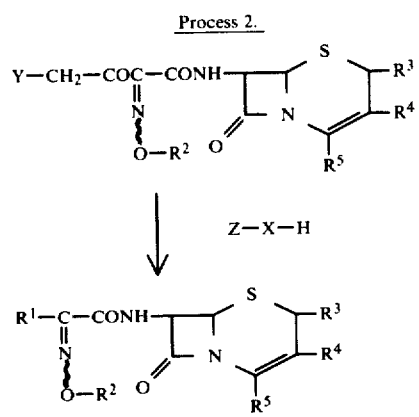

wherein
$R^1$, $R^2$, $R^3$, $R^4$, $R^5$ and X are each as defined above,
Y is an acid residue, and
Z is 2-mercaptoethyl, lower alkoxy(thiocarbonyl) or 2-mercaptophenyl.

Process 3.

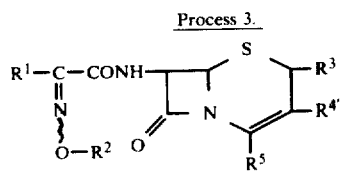

-continued
Process 3.

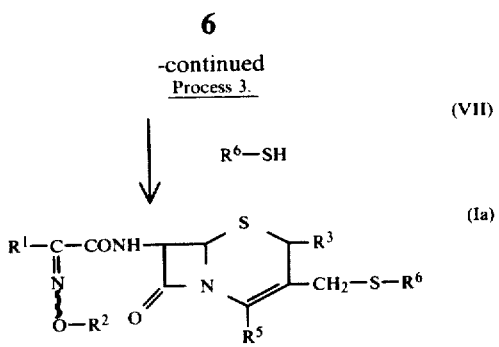

wherein
$R^1$, $R^2$, $R^3$ and $R^5$ are each as defined above,
$R^{4'}$ is acyloxymethyl, and
$R^6$ is heterocyclic group which may be substituted with lower alkyl.

Process 4.

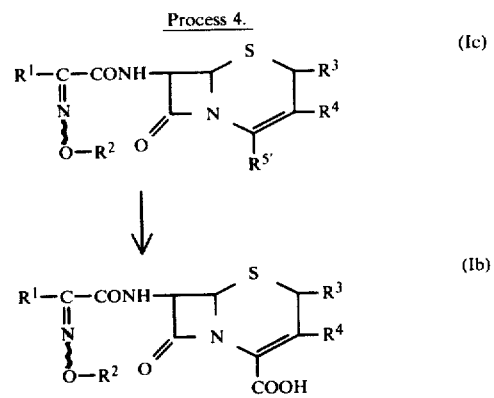

wherein
$R^1$, $R^2$, $R^3$ and $R^4$ are each as dfined above, and
$R^{5'}$ is derivative of carboxy group.

The starting compound (III) to be used in the Process 1 are novel and can be prepared by the processes as illustrated in the following scheme.

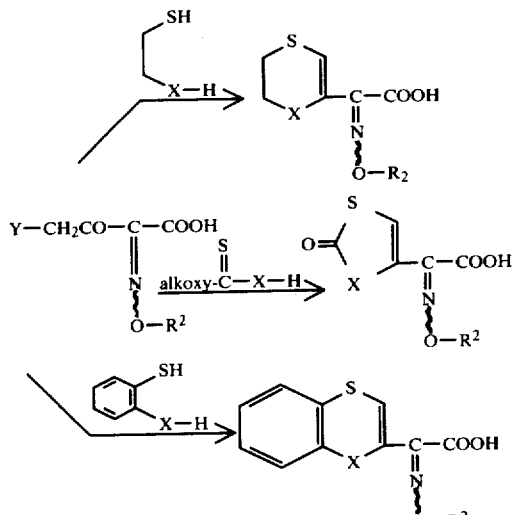

wherein $R^2$, X and Y are each as defined above.

More particularly, for example, 2-(2,3-dihydro-1,4-oxathiin-6-yl)-2-methoxyiminoacetic acid (syn isomer)

can be prepared by reacting 2-mercaptoethanol with ethyl 2-chloroacetyl-2-methoxyiminoacetate (syn isomer) (alternatively named as ethyl 4-chloro-3-oxo-2-methoxyiminobutyrate (syn isomer), and then hydrolyzing the resultant product. The other starting compounds (III) can also be prepared in a similar manner to the above method, and particular preparation therefor will be mentioned below in "Preparation of the starting compund".

The processes for preparing the object compounds (I) will be explained in detail in the following.

PROCESS 1

The object compound (I) and the salt thereof can be prepared by reacting a compound (II), its reactive derivative at the amino group or a salt thereof with a disubstituted acetic acid (III), its reactive derivative at the carboxy group or a salt thereof.

Suitable reactive derivative at the amino group of the compound (II) may include a conventional reactive derivative used in amidation, for example, a silyl derivative formed by the reaction of the compound (II) with a silyl compound such as bis(trimethylsilyl)acetamide, trimethylsilylacetamide, etc.; isocyanato, isothiocyanato, etc.; Schiff's base or its tautomeric enamine type isomer formed by the reaction of the compound (II) with an aldehyde compound (e.g., acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc.) or a ketone compound (e.g., acetone, methyl ethyl ketone, methyl isobutyl ketone, acetylacetone, ethyl acetoacetate, etc.), and the like.

Suitable salts of the compound (II) are to be referred to the ones exemplified hereinabove for the compound (I).

Suitable salts of the compound (III) may include a salt with an inorganic base such as an alkali metal salt (e.g., sodium salt, potassium salt, etc.), an alkaline earth metal salt (e.g., calcium salt, magnesium salt, etc.), a salt with an organic base such as trimethylamine, triethylamine, and the like.

Suitable reactive derivatives at the carboxy group of the compound (III) may include, for example, an acid halide, an acid anhydride, an activated amide, an activated ester, and the like, and preferably acid chloride, acid bromide;

a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid, trichloroacetic acid, etc.), aromatic carboxylic acid (e.g., benzoic acid, etc.); a symmetrical acid anhydride; an activated acid amide with imidazole, 4-substituted imidazole, dimethylpyrazole, triazole or tetrazole;

an activated ester (e.g., cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, an ester with N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like. The suitable reactive derivative can be optionally selected from the above according to the kind of the compound (III) to be used practically.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other organic solvent which does not adversely influence to the reaction. Among these solvents, hydrophilic solvents may be used in a mixture with water.

When the disubstituted acetic acid (III) is used in a form of the free acid or salt in this reaction, the reaction is preferably carried out in the presence of a conventional condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropoyl)carbodiimide, N,N'-carbonylbis(2-methylimidazole), pentamethyleneketene-N-cyclohexylimine, diphenylketene-N-cyclohexylimine, ethoxyacetylene, β-chlorovinylethyl ether, 1-(4-chlorobenzenesulfonyloxy)-6-chloro-1H-benzotriazole, trialkyl phosphite, ethyl polyphosphate, isopropyl polyphosphate, phosphorus oxychloride, phosphorus trichloride, thionyl chloride, oxalyl chloride, triphenylphosphine, N-ethylbenzisoxazolium salt, N-ethyl-5-phenyl-isoxazolium-3'-sulfonate, Vilsmeier reagent prepared by the reaction of dimethylformamide with thionyl chloride, phosphorus oxychloride, phosgene or the like.

In the present reaction as explained above, it is to be noted that, in case that the starting compound (III) is reacted with the compound (II) or its reactive derivative at the amino group or the salt thereof in the presence of, for example, phosphorus pentachloride, thionyl chloride, etc., an anti isomer of the object compund (I) or a mixture of the anit isomer and syn isomers thereof may be usually isolated and a syn isomer of the object compound (I) may be rather hardly isolated as a sole product even if a syn isomer of the starting compound (III) is used. It may be understood that the tendency of such an isomerization in the reaction conducted by the method as explained above is due to the fact that the less stable syn isomer tends to isomerize partially or wholly to the corresponding more stable anti isomer in the course of such reaction, for example, in so-called activation step of the compound (III) so that more stable isomer, i.e. the anti isomer of the object compound (I) is isolated as the reaction product.

Accordingly, in order to obtain a syn isomer of the object compound (I) selectively and in high yield, it is necessary to use a syn isomer of the starting compound (III), and to conduct the reaction in the selected reaction condition. That is, a syn isomer of the object compound (I) can be obtained more selectively and in higher yield by conducting the reaction of the compound (II) with a syn isomer of the starting compound (III) preferably, for example, in the presence of a Vilsmeier reagent as mentioned above and under around neutral condition.

PROCESS 2

The object compound (I) and the salt thereof can also be prepared by reacting a compound (IV) or its salt with a compound (V) or its salt.

"Acid residue" for Y of the starting compound (IV) may be halogen (e.g. chlorine, bromine, iodine or fluorine,), tosylate, mesylate, or the like, preferably halogen.

Suitable salt of the compound (IV) may be the same as that of the compounds (II).

Suitable salt of the compound (V) may include an alkali metal salt (e.g., sodium salt, potassium salt, etc.), an inorganic acid salt (e.g., hydrochloride, etc.), and the like.

Suitable example of "lower alkoxy(thiocarbonyl)" for Z may include methoxy(thiocarbonyl), ethoxy(thiocarbonyl), propoxy(thiocarbonyl), isopropoxy(thiocarbonyl), butoxy(thiocarbonyl), t-butoxy(thiocarbonyl), pentyloxy(thiocarbonyl), hexyloxy(thiocarbonyl), and the like, more preferably methoxy(thiocarbonyl) or ethoxy(thiocarbonyl).

The reaction is usually carried out in a solvent such as water, alcohol (e.g., methanol, ethanol, propanol, butanol, etc.), N.N-dimethylformamide, dimethylsulfoxide, tetrahydrofuran, dioxane, acetonitrile or any other solvent which does not adversely influence to the reaction. The reaction temperature is not critical and the reaction is preferably conducted within the range of heating to ambient temperature.

In this reacton, in order to obtain a syn isomer of the object compound (I) selectively, it may be preferable to conduct the reaction by using a syn isomer of the starting compound (IV) under mild conditions. Further, it is to be noted that the reaction may be conducted preferably in the presence of a dehydrating agent.

PROCESS 3

The object compound (Ia) and the salt thereof can be prepared by reacting a compound (VI) or its salt with a compound (VII) or its reactive derivative at the mercapto group.

The starting compound (VI) to be used in the present process can be prepared by reacting the compound (II) wherein $R^4$ is acyloxymethyl, its reactive derivative at the amino group or its salt with the compound (III), its reactive derivative at the carboxy group or its salt under substantially the same reaction conditions as those for preparing the compound (I) as stated in the explanation of the above Process 1.

Suitable reactive derivative at the mercapto group of the compound (VII) may include a metal salt such as an alkali metal salt (e.g., sodium salt, potassium salt, etc.), an alkaline earth metal salt (e.g., magnesium salt, etc.), and the like.

The reaction may be preferably carried out in a solvent such as water, acetone, chloroform, nitrobenzene, N,N-dimethylformamide, metanol, ethanol, dimethylsulfoxide or any other organic solvent which does not adversely influence to the reaction or an optional mixture thereof, preferably in a rather high polar solvent. The reaction is preferably carried out under around neutral condition. When the compound (VI) or the compound (VII) is used in a free form, the reaction is preferably conducted in the presence of a base such as alkali metal hydroxide, alkali metal carbonate, alkali metal bicarbonate, trialkylamine or the like. The reaction is usually carried out at ambient temperature or slightly elevated temperature.

Process 4

The object compound (Ib) can be prepared by subjecting a compound (Ic) to a reaction for transforming a derivative of carboxy group into carboxy group.

Suitable examples of the derivative of carboxy group for $R^{5'}$ are referred to those as illustrated hereinabove for $R^5$ of the compound (I).

The present invention is carried out by conventional method, such as hydrolysis, reduction or the like.

Suitable acid for the hydrolysis includes an organic or an inorganic acid, for example, formic acid, trifluoroacetic acid, benzenesulfonic acid, p-toluenesulfonic acid, hydrochloric acid and the like. Preferable acid is one which can easily be removed from the reaction mixture by a conventional manner such as distillation under reduced pressure, for example, formic acid, trifluoroacetic acid, hydrochloric acid, etc. The acidic hydrolysis can be carried out preferably in the presence of a solvent. Suitable solvent includes a conventional organic solvent, water or a mixture thereof.

The basic hydrolysis is conducted in the presence of a base. Suitable base includes, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.) alkali metal bicarbonate (e.g., sodium bicarbonate, potassium bicarbonate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as alkali metal acetate (e.g., sodium acetate, potassium acetate, etc.), alkali metal alkoxide (e.g., sodium methoxide, sodium ethoxide, sodium propoxide, etc.), trialkylamine (e.g., trimethylamine, triethylamine, etc.), picoline, N-methylpyrrolidine, N-methylmorpholine, 1,5-diazabicyclo[4,3,0]-5-nonene, 1,4-diazabicyclo[2,2,2]octane, 1,5-diazabicyclo[5,4,0]-7-undecene or the like. The basic hydrolysis is often and preferably carried out in water or a hydrophilic or moistened organic solvent or a mixture thereof. The reduction may be conducted with a conventional reducing agent which is used for transforming the derivative of carboxy group to a carboxy group, for example, an alkali metal borohydride (e.g., sodium borohydride, etc.) palladium carbon, palladium oxide, platinum oxide, and the like.

The reaction temperature is not critical and may be suitably selected in accordance with the kind of the derivative of carboxy group and the method to be applied, and the present reaction is preferably carried out under a mild condition such as under cooling, at ambient temperature or slightly elevated temperature.

As to the object compound (I) prepared according to the foregoing processes, in case that the compound (I) is a compound wherein X is a substituted imino group, said compound can be subjected to elimination reaction for eliminating a substituent of the substituted imino group for X thereof by a well known conventional method such as hydrolysis, reduction or the like to provide the compound (I) wherein X is an imino group. The methods of hydrolysis and reduction and the reaction conditions (e.g., reaction temperature, solvent, etc.)

are substantially the same as those illustrated in the foregoing Process 4.

In case that the object compound (I) has a free carboxy group at 4-position and/or a free imino group for X, it may be transformed into its pharmaceutically acceptable salt by a conventional method.

And further, in case that the compound (I) obtained in accordance with the process as explained above is a free carboxylic acid or its salt, it may be converted to the corresponding ester thereof. The esterification reaction is carried out by a conventional method in a solvent which does not adversely influence the reaction, for example, N,N-dimethylformamide, dioxane, acetonitrile, chloroform, methylene chloride, ethylene chloride, tetrahydrofuran, ethyl acetate or the like. The reaction temperature is not critical, but the reaction is preferably conducted within the range of cooling to an ambient temperature.

Further, it is to be noted that the present invention may include, within its scope, the cases that the substituted imino and/or the derivative at the carboxy group are transformed into the corresponding free imino group and/or carboxy group during the reaction of post-treatment in the processes as explained above.

The object compound (I) obtained according to the processes as explained above can be isolated and purified in a conventional manner.

As mentioned hereinabove, there is isomerization between "syn isomer" and "anti isomer" in the object compounds (I) and the starting compound (III) and the equilibrium trends to more stable anti-isomer. Accordingly, in the course of the aforementioned processes for preparation of the object compound (I) including the isolation and purification steps, said isomerization may occur and an anti-isomer of the object compound (I) may be ocassionally isolated as the final main product even when an syn-isomer of the compound (III), (IV), (VI) or (Ic) is used as a starting compound. Therefore, it is to be noticed that, in case of preparing an syn-isomer of the object compound (I) by the reaction of a compound (II) with a compound (III), the said reaction of the compound (II) with an syn-isomer of the compound (III) is to be conducted preferably in the presence of the aforementioned Vilsmeier reagent which is more preferred condensing agent for preventing undesired geometrical isomerization as mentioned above.

Further, it is to be noted that, in the afore-mentioned reaction and/or the post-treating of the reaction mixture the aforementioned tautomeric isomer may be occasionally transformed into the other tautomeric isomer and such case is also included in the scope of the present invention.

In case that a mixture of the syn isomer and anti isomer of the object compound (I) is obtained, they can be separated by a conventional method such as column chromatography on silica gel, heigh pressure liquid chromatography, fractional recrystallization, selective hydrolysis, or the like.

The object compound (I) or pharmaceutically acceptable salt thereof of the present invention is a novel compounds which exhibit high antibacterial activities, inhibiting the growth of a wide variety of pathogenic microorganisms including Gram-positive and Gram-negative bacteria and is useful as antibacterial agent. Particularly, it is to be noted that an syn isomer of the object compound (I) has much higher antibacterial activities than the corresponding anti isomer of the compound (I), and accordingly a syn isomer of the object compound (I) is characterized by having much superiority to the corresponding anti isomer in the therapeutic value.

Now in order to show the utility of the object compound (I), the test data of some representative compounds (I) are shown in the following.

IN VITRO ANTIBACTERIAL ACTIVITY:

1. Test Method

In vitro antibacterial activity was determined by the two-fold agar-plate dilution method as described below.

One loopful of an overnight culture of each test strain in Trypticase-soy broth (approximately $10^6$ viable cells per ml.) was streaked on heart infusion agar (III-agar) containing graded concentrations of antibiotics, and the minimal inhibitory concentration (MIC) was expressed in terms of $\mu g./ml.$ after incubation at 37° C. for 20 hours.

2. Test Compounds

No. 1

7-[2-(2,3-dihydro-1,4-oxathiin-6-yl)-2-methoxyiminoacetamido]cephalosporanic acid (syn isomer)

No. 2

7-[2-(2,3-dihydro-1,4-oxathiin-6-yl)-2-methoxyiminoacetamido]-3-(1-methyl-1H-tetrazol-5-yl)thiomethyl-3-cephem-4-carboxylic acid (syn isomer)

No. 3

7-[2-(2,3-dihydro-1,4-oxathiin-6-yl)-2-methoxyiminoacetamido]-3-carbamoyloxymethyl-3-cephem-4-carboxylic acid (syn isomer)

No. 4

7-[2-(2,3-dihydro-1,4-dithiin-5-yl)-2-methoxyiminoacetamido]-3-(1,3,4-thiadiazol-2-yl)thiomethyl-3-cephem-4-carboxylic acid (syn isomer)

No. 5

7-[2-(2,3-dihydro-1,4-dithiin-5-yl)-2-methoxyiminoacetamido]-3-cephem-4-carboxylic acid (syn isomer)

3. Test Results

MIC ($\mu g/ml.$)

| Strain | Compound No. | | | | |
| --- | --- | --- | --- | --- | --- |
|  | 1 | 2 | 3 | 4 | 5 |
| Staphylococcus aureus 209-P JC-1 | 3.13 | 3.13 | 6.25 | 0.39 | 6.25 |
| Proteus vulgaris LAM-1025 | 12.5 | 25 | 100 | 6.25 | 3.13 |
| Pseudomonas aeruginose NCTC-10490 | 25 | 12.5 | 50 | 50 | 400 |
| Esherichia coli 327 | 0.78 | 0.2 | 0.78 | 0.78 | — |
| Proteus mirabilis 525 | 0.78 | 0.78 | 0.78 | 3.13 | — |

For therapeutic administration, the object compound (I) of the present invention is used in the form of conventional pharmaceutical preparation which contains said compound, as an active ingredient, in admixture with pharmaceutically acceptable carriers such as an organic or inorganic solid or liquid excipient which is suitable for oral, parenteral or external administration.

The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age, conditions of the patient, a kind of disease, a kind of the compound (I) to be applied, etc., an average single dose of about 50 mg., 100 mg., 250 mg., and 500 mg. of the object compound (I) of the present invention has proved to be effective in treating diseases infected by pathogenic bacteria.

In general, amounts between 1 mg. and about 1000 mg. or even more may be administered to a patient.

The following examples are given for the purpose of illustrating the present invention:

SEPARATION OF THE STARTING COMPOUNDS

EXAMPLE A.

2-(2,3-Dihydro-1,4-oxathiin-6-yl)-2-methoxyiminoacetic acid (syn isomer)

(i) A solution of ethyl 2-chloroacetyl-2-methoxyiminoacetate (65 g.) in dry chloroform (130 ml.) was added to a stirred mixture of 2-mercaptoethanol (25 g.), triethylamine (35 g.) and dry chloroform (70 ml.) at 20° C. over 30 minutes, and stirred at the same temperature for 2.5 hours. After the solution was adjusted to pH 1.0 with 10% hydrochloric acid under ice cooling, the chloroform layer was separated, washed with water twice and dried over magnesium sulfate. The solution was concentrated in vacuo at 40° C. to give yellow oil. The oil was dissolved in toluene (600 ml.), and then p-toluenesulfonic acid (5.5 g.) was added to the toluene solution. The solution was heated under reflux for 2 hours while removing the produced water. The resultant solution was allowed to cool at room temperature and filtered. The filtrate was washed with water (100 ml.) three times, a saturated aqueous solution of sodium bicarbonate (100 ml.) twice and water (100 ml.) twice in turn, and then dried over magnesium sulfate. The solution was concentrated under reduced pressure. The residue was subjected to column chromatography on silica gel "Kieselgel 60" [Trademark: manufactured by E. Merck] (1 kg.) and eluted with benzene. After the eluate was concentrated under reduced pressure, the residue was washed with diisopropyl ether and dried to give ethyl 2-(2,3-dihydro-1,4-oxathiin-6-yl)-2-methoxyiminoacetate (syn isomer, 21 g.), pale yellow crystals, mp. 64° to 66° C.

I.R. $\nu_{max}^{Nujol}$: 1715, 1650, 1620, cm$^{-1}$.

N.M.R. δ(DMSO-d$_6$, ppm): 1.25 (3H, t, J=7 Hz), 3.13 (2H, t, J=4 Hz), 3.83 (3H, s), 4.15~4.40 (4H, m), 5.88 (1H, s).

(ii) 1 N Aqueous solution (24 ml.) of sodium hydroxide was added to a solution of ethyl 2-(2,3-dihydro-1,4-oxathiin-6-yl)-2-methoxyiminoacetate (syn isomer, 4.6 g.) in methanol (50 ml.), and stirred at room temperature for 16 hours. After the resultant solution was concentrated in vacuo, the residue was dissolved in water. The solution was washed with ethyl acetate and adjusted to pH 1.0 with 10% hydrochloric acid. The solution was extracted with ethyl acetate, and the extract was washed with water and dried over magnesium sulfate. The solution was concentrated under reduced pressure at 40° C., and the residue was washed with diisopropyl ether and then dried to give 2-(2,3-dihydro-1,4-oxathiin-6-yl)-2-methoxyiminoacetic acid (syn isomer, 3.8 g.), white crystals, mp. 129° to 131° C. (dec.).

I.R. $\nu_{max}^{Nujol}$: 2550~2600, 1725, 1650, 1620 cm$^{-1}$.

N.M.R. δ(DMSO-d$_6$, ppm): 3.06 (2H, t, J=4 Hz), 3.80 (3H, s), 4.18 (2H, t, J=4 Hz), 5.80 (1H, s).

EXAMPLE B 2-(2,3-Dihydro-1,4-oxathiin-6-yl)-2-methoxyiminoacetic acid (anti isomer)

(i) To a stirred solution of 2-mercaptoethanol (7.8 g.) and ethyl 2-(2-chloroacetyl)-2-methoxyiminoacetate (2.08 g.) in dry chloroform (200 ml.) was added a solution of triethylamine (11 g.) in dry chloroform (30 ml.) at 20° C., and stirred at the same temperature for 3 hours. The resultant solution was washed with 10% hydrochloric acid twice, a saturated aqueous solution of sodium hydroxide twice and water twice in turn, and dried over magnesium sulfate. The solution was concentrated in vacuo at 40° C., and the residue was dissolved in dry toluene (200 ml.). After adding p-toluenesulfonic acid (3 g.) to the solution, the solution was heated under reflux for 30 minutes while removing the produced water. The resultant solution was allowed to cool at room temperature and treated with activated charcoal, and then ethyl acetate (150 ml.) was added thereto. The solution was washed with a saturated aqueous solution of sodium bicarbonate and water twice in turn dried over magnesium sulfate, and then concentrated in vacuo at 40° C. to give ethyl 2-(2,3-dihydro-1,4-oxathiin-6-yl)-2-methoxyiminoacetate (mixture of syn isomer and anti isomer, 18.5 g.), yellow oil.

I.R. $\nu_{max}^{Nujol}$: 2800~2900, 1715, 1620 cm$^{-1}$.

(ii) A mixture of ethyl 2-(2,3-dihydro-1,4-oxathiin-6-yl)-2-methoxyiminoacetate (16 g.), methanol (160 ml.) and a 1 N aqueous solution (85 ml.) of sodium hydroxide was stirred at room temperature for 25 minutes. The resultant solution was adjusted to pH 4.5 with 10% hydrochloric acid and concentrated at 40° C. in vacuo. To the residue was added ethyl acetate, and the solution was adjusted to pH 7.5 with a saturated aqueous solution of sodium bicarbonate, and then shaken sufficiently. The organic layer was separated and extracted with a saturated aqueous solution of sodium bicarbonate. The extract and the aqueous layer were combined together and adjusted to pH 1.0 with 10% hydrochloric acid. The solution was extracted with ethyl acetate, and the extract was washed with water and then dried over magnesium sulfate. After the solution was concentrated in vacuo, the residue was washed with diisopropyl ether to give 2-(2,3-dihydro-1,4-oxathiin-6-yl)-2-methoxyiminoacetic acid (anti isomer, 3.5 g.), yellow crystals, mp. 108° to 110° C. (dec.).

I.R. $\nu_{max}^{Nujol}$: 2550~2650, 1695, 1620, 1600 cm$^{-1}$.

N.M.R. δ(DMSO-d$_6$, ppm): 3.06 (2H, t, J=5 Hz), 4.20 (2H, t, J=5 Hz), 4.89 (3H, s), 6.43 (1H, s).

EXAMPLE C 2-(2,3-Dihydro-1,4-dithiin-6-yl)-2-methoxyiminoacetic acid (syn isomer)

(i) Ethane-1,2-dithiol (20.6 g.) was allowed to react with ethyl 2-chloroacetyl-2-methoxyiminoacetate (41.4 g.) in a similar manner to that of Example A—(i) to give ethyl 2-(2,3-dihydro-1,4-dithiin-6-yl)-2-methoxyiminoacetate (syn isomer, 11 g.), white crystals, mp. 65° to 67° C.

I.R. $\nu_{max}^{Nujol}$: 1725, 1670 cm$^{-1}$.

N.M.R. δ(DMSO-d$_6$, ppm): 1.25 (3H, t, J=7 Hz), 3.25 (4H, s), 3.80 (3H, s), 4.30 (2H, q, J=7 Hz), 6.78 (1H, s).

(ii) Thus obtained ethyl 2-(2,3-dihydro-1,4-dithiin-6-yl)-2-methoxyiminoacetate (syn isomer, 2.47 g.) was hydrolyzed in a similar manner to that of Example A—(ii) to give 2-(2,3-dihydro-1,4-dithiin-6-yl)-2-methoxyiminoacetic acid (syn isomer, 2.0 g.), white crystals, mp. 120° to 122° C. (dec.).

I.R. $\nu_{max}^{Nujol}$: 2500~2600, 1720, 1670, 1620 cm$^{-1}$.

N.M.R. δ(DMSO-d$_6$, ppm): 3.20 (4H, s), 3.80 (3H, s), 6.61 (1H, s).

EXAMPLE D 2-(4-Formyl-2,3-dihydro-4H-1,4-thiazin-5-yl)-2-methoxyiminoacetic acid (syn isomer)

(i) To a stirred solution of 2-mercaptoethylamine hydrochloride (10.0 g.) in chloroform (100 ml.) were added triethylamine (18.7 g.) and ethyl 2-chloroacetyl-2-methoxyiminoacetate (26.2 g., purity 70%) under ice-cooling and stirred at room temperature for 1.5 hours. After the resultant solution was concentrated in vacuo, water was added to the residue and extracted with diethyl ether four times. The extract was washed with a saturated aqueous solution of sodium chloride, and extracted with 10% hydrochloric acid 4 times. The hydrochloric acid extract was washed with diethyl ether twice and adjusted to pH 6.5 with a saturated aqueous solution of sodium bicarbonate, and further extracted with diethyl ether 4 times. The extract was dried over magnesium sulfate and concentrated in vacuo to give ethyl 2-(2,3-dihydro-4H-1,4-thiazin-5-yl)-2-methoxyiminoacetate (syn isomer, 5.2 g.), oil.

I.R. $\nu_{max}^{Nujol}$: 3400 (shoulder), 1740, 1635 cm$^{-1}$.

N.M.R. δ(CCl$_4$, ppm): 1.36 (3H, t, J=7 Hz), 2.9~3.2 (2H, m), 3.5~3.8 (2H, m) 3.89 (3H, s), 4.30 (2H, q, J=7 Hz), 5.00 (1H, s).

(ii) Ethyl 2-(2,3-dihydro-4H-1,4-thiazin-5-yl)-2-methoxyiminoacetate (syn isomer, 5.8 g.) was added to a mixture of acetic anhydride (7.7 g.) and formic acid (3.48 g.), which was warmed at 50° C. for 2 hours previously, under ice-cooling, and stirred at room temperature overnight. After adding chilled water (100 ml.) to the resultant solution, the solution was extracted with ethyl acetate three times. The extract was washed with a saturated aqueous solution of sodium chloride once, an aqueous solution of sodium bicarbonate four times and a saturated aqueous solution of sodium chloride once in turn, and dried over magnesium sulfate. The solution was concentrated in vacuo, and the residue was triturated with diisopropyl ether (15 ml.). The crystals were collected by filtration and washed with diisopropyl ether to give ethyl 2-(4-formyl-2,3-dihydro-4H-1,4-thiazin-5-yl)-2-methoxyiminoacetate (syn isomer, 5.0 g.), mp. 94° to 96° C.

I.R. $\nu_{max}^{Nujol}$: 1735, 1725, 1675 cm$^{-1}$.

N.M.R. δ(CDCl$_3$, ppm): 3.16 (3H, t, J=7 Hz), 3.95 (3H, s), 2.96~3.28 (2H, m), 3.78~4.20 (2H, m), 4.38 (2H, q, J=7 Hz), 6.15 (1H, s), 8.62 (1H, s).

(iii) To a suspension of thus obtained ethyl 2-(4-formyl-2,3-dihydro-4H-1,4-thiazin-5-yl)-2-methoxyiminoacetate (syn isomer, 4.8 g.) in ethanol (48 ml.) was added 1 N aqueous solution of potassium hydroxide (22.3 ml.), and the mixture was stirred at room temperature for 1.25 hours. After removing ethanol from the resultant solution under reduced pressure, water was added to the residue to a total volume of 100 ml., and washed with diethyl ether. The solution was adjusted to pH 1 with 10% hydrochloric acid, and salted out. After the solution was extracted with ethyl acetate, the extract was washed with a saturated aqueous solution of sodium chloride, dried over magnesium sulfate and concentrated in vacuo. The residue was triturated with diethyl ether (15 ml.) and the crystals were collected by filtration and washed with diethyl ether to give 2-(4-formyl-2,3-dihydro-4H-1,4-thiazin-5-yl)-2-methoxyiminoacetic acid (syn isomer, 3.51 g.).

I.R. $\nu_{max}^{Nujol}$: 1710, 1610 cm$^{-1}$.

N.M.R. δ(DMSO-d$_6$, ppm): 3.08 (2H, m), 3.80 (2H, m), 3.83 (3H, s), 6.40 (1H, s), 8.47 (1H, s).

EXAMPLE E 2-(2-Oxo-1,3-dithiol-4-yl)-2-methoxyiminoacetic acid (syn isomer and anti isomer)

(i) Ethyl 2-chloroacetyl-2-methoxyiminoacetate (31.2 g.) was added dropwise to a solution of sodium o-ethyl xanthogenate (31 g.) in water (150 ml.), and stirred at 15° C. for an hour. After removing methanol from the resultant solution in vacuo, the residue was extracted with benzene to give ethyl 2-ethoxy(thiocarbonyl)thioacetyl-2-methoxyiminoacetate.

I.R. $\nu_{max}^{Nujol}$: 1735, 1700, 1593 cm$^{-1}$.

N.M.R. δ(CCl$_4$, ppm): 1.30 (3H, t, J=7 Hz), 1.40 (3H, t, J=7 Hz), 4.12 (3H, s), 4.25 (2H, q, J=7 Hz), 4.32 (2H, s), 4.58 (2H, q, J=7 Hz).

A mixture of thus obtained ethyl 2-ethoxy(thiocarbonyl)thioacetyl-2-methoxyiminoacetate (41 g.), conc. sulfuric acid (8 ml.) and benzene (300 ml.) was heated under reflux for 2 hours while removing the produced water. The resultant solution was washed with water, an aqueous solution of sodium bicarbonate and water in turn, and then dried over magnesium sulfate. The solution was treated with activated charcoal, and the solvent was removed in vacuo to give ethyl 2-(2-oxo-1,3-dithiol-4-yl)-2-methoxyiminoacetate (34.3 g.). This product was subjected to column chromatography on silica gel [eluent: benzene] to give the syn isomer (13.5 g.) and the anti isomer (8.5 g.) separately.

Syn isomer

I.R. $\nu_{max}^{film}$: 1735, 1710, 1650 cm$^{-1}$.

N.M.R. δ(DMSO-d$_6$, ppm): 1.35 (3H, t, J=7 Hz), 3.95 (3H, s), 4.34 (2H, q, J=7 Hz), 7.63 (1H, s).

Anti isomer

I.R. $\nu_{max}^{film}$: 1740, 1720, 1640 cm$^{-1}$.

N.M.R. δ(DMSO-d$_6$, ppm): 1.30 (3H, t, J=7 Hz), 4.08 (3H, s), 4.33 (2H, q, J=7 Hz), 8.00 (1H, s).

(ii) To a solution of thus obtained ethyl 2-(2-oxo-1,3-dithiol-4-yl)-2-methoxyiminoacetate (anti isomer, 1.7 g.) in ethanol (20 ml.) was added dropwise a solution of sodium carbonate 10 hydrate (2.2 g.) in water (10 ml.) and the mixture was stirred at room temperature for 3 hours. After removing ethanol from the resultant solution in vacuo, the residue was acidified with hydrochloric acid and extracted with diethyl ether. The extract was washed with a saturated aqueous solution of sodium chloride, dried over magnesium sulfate, and concentrated in vacuo to give oily product The oil was allowed to stand in a refrigerator to give 2-(2-oxo-1,3-dithiol-4-yl)-2-methoxyiminoacetic acid (anti isomer, 0.75 g.).

I.R. $\nu_{max}^{Nujol}$: 3270, 1730, 1625 cm$^{-1}$.

N.M.R. δ(DMSO-d$_6$, ppm): 4.02 (3H, s), 8.0 (1H, s).

(iii) To a solution of ethyl 2-(2-oxo-1,3-dithiol-4-yl)-2-methoxyiminoacetate (syn isomer, 1 g.) in tetrahydrofuran (10 ml.) and ethanol (20 ml.) was added a solution of sodium carbonate 10 hydrate (1.3 g.) in water (20 ml.), and the mixture was stirred at room temperature for 3 hours. After the solvent was removed in vacuo, the residue was washed with diethyl ether, adjusted to pH 2 and extracted with diethyl ether. The extract was washed with a saturated aqueous solution of sodium chloride, dried over magnesium sulfate and concentrated in vacuo to give 2-(2-oxo-1,3-dithiol-4-yl)-2-methoxyiminoacetic acid (syn isomer, 0.2 g.).

I.R. $\nu_{max}^{film}$: 1725, 1625 cm$^{-1}$.

N.M.R. $\delta$(DMOS-d$_6$, ppm): 3.93 (3H, s), 7.57 (1H, s).

EXAMPLE F 2-(1,4-Benzoxathiin-2-yl)-2-methoxyiminoacetic acid (syn isomer)

(i) 2-Mercaptophenol (3.5 g.) was allowed to react with ethyl 2-chloroacetyl-2-methoxyiminoacetate (6.2 g.) in a similar manner to that of Example A—(i) to give ethyl 2-(1,4-benzoxathiin-2-yl)-2-methoxyiminoacetate (syn isomer, 1.2 g.), pale yellow crystals, mp. 78° to 80° C.

I.R. $\nu_{max}^{Nujol}$: 3050, 1725, 1600 cm$^{-1}$.

N.M.R. $\delta$(DMSO-d$_6$, ppm): 1.25 (3H, t, J=7 Hz), 3.92 (3H, s), 4.33 (2H, q, J=7 Hz), 6.25 (1H, s), 7.24 (4H, m).

(ii) Thus obtained ethyl 2-(1,4-benzoxathiin-2-yl)-2-methoxyiminoacetate (syn isomer, 1.2 g.) was hydrolyzed in a similar manner to that of Example A—(ii) to give 2-(1,4-benzoxathiin-2-yl)-2-methoxyiminoacetic acid (syn isomer, 0.9 g.), mp. 143° to 145° C. (dec.).

I.R. $\nu_{max}^{Nujol}$: 2600~2500, 1735, 1600 cm$^{-1}$.

N.M.R. $\delta$(DMSO-d$_6$, ppm): 3.90 (3H, s), 6.15 (1H, s), 6.8~7.2 (4H, m).

EXAMPLE G 2-(1,4-Benzodithiin-2-yl)-2-methoxyiminoacetic acid (syn isomer)

(i) o-Benzenedithiol (7.1 g.) was allowed to react with ethyl 2-chloroacetyl-2-methoxyiminoacetate (11.4 g.) in a similar manner to that of Example A—(i) to give ethyl 2-(1,4-benzodithiin-2-yl)-2-methoxyiminoacetate (syn isomer, 1.0 g.), yellow crystals, mp. 78° to 81° C.

I.R. $\nu_{max}^{Nujol}$: 1725, 1620, 1600 cm$^{-1}$.

N.M.R. $\delta$(DMSO-d$_6$, ppm): 1.20 (3H, t, J=7 Hz), 3.90 (3H, s), 4.20 (2H, q, J=7 Hz), 7.03 (1H, s), 7.2~7.5 (4H, m).

(ii) Thus obtained ethyl 2-(1,4-benzodithin-2-yl)-2-methoxyiminoacetate (syn isomer, 1.0 g.) was hydrolyzed in a similar manner to that of Example A—(ii) to give 2-(1,4-benzodithiin-2-yl)-2-methoxyiminoacetic acid (syn isomer, 0.8 g.)

I.R. $\nu_{max}^{film}$: 2550~2600, 1735, 1650, 1625, 1600 cm$^{-1}$.

N.M.R. $\delta$(DMSO-d$_6$, ppm): 3.9 (3H, s), 7.00 (1H, s), 7.2~7.5 (4H, m).

EXAMPLE H (i) 4-Nitrobenzyl 7-amino-3-cephem-4-carboxylate (5 g.) was dissolved in a solution of trimethylsilylacetamide (13.8 g.) and bis(trimethylsilyl)acetamide (10 ml.) in dry ethyl acetate (50 ml.) and stirred at 45° C. for 1.5 hours. A solution of bromine (2.88 g.) in methylene chloride (7 ml.) was added dropwise to a solution of diketene (1.5 g.) in methylene chloride (7 ml.) at −40° C. over 20 minutes and stirred at −30° C. for 1 hour.

The solution obtained thus was added to dropwise to the above solution of 4-nitrobenzyl 7-amino-3-cephem-4-carboxylate under cooling at −15° C. and then stirred at the same temperature for 30 minutes. Water (50 ml.) was added to the resultant solution and extracted with ethyl acetate. The ethyl acetate extract was washed with water, dried over magnesium sulfate and concentrated under reduced pressure to give oily 4-nitrobenzyl 7-[2-(2-bromoacetyl)acetamido]-3-cephem-4-carboxylate (6.15 g.).

I.R. $\nu_{max}^{Nujol}$: 1780, 1740, 1630 cm$^{-1}$.

N.M.R. $\delta$(DMSO-d$_6$, ppm): 3.62 (2H, broad s), 4.37 (2H, s), 5.08 (1H, d, J=5 Hz), 5.40 (2H, s), 5.77~6.05 (m), 6.67 (1H, t, J=5 Hz), 7.68, 8.04 (4H, m, J=9 Hz), 9.07 (1H, d, J=8 Hz).

(ii) 4-Nitrobenzyl 7-[2-(2-bromoacetyl)acetamido]-3-cephem-4-carboxylate (8.40 g.) was suspended in a mixture of tetrahydrofuran (150 ml.) and water (30 ml.). To the suspension were added acetic acid (50 ml.) and a solution of sodium nitrite (1.20 g.) in water (15 ml.) under ice-cooling, and stirred at 20° to 22° C. for 1.5 hours. The resultant solution was poured into ice-water (300 ml.) and stirred for 20 minutes. The precipitating substance was collected by filtration, washed with water, dried and then recrystallized from ethyl acetate to give 4-nitrobenzyl-7-[2-(2-bromoacetyl)-2-hydroxyiminoacetamido]-3-cephem-4-carboxylate (syn-isomer: 3.1 g.), mp. 153° to 162° C.

I.R. $\nu_{max}^{Nujol}$: 3250, 1780, 1720, 1705, 1650, 1610, 1600 (shoulder), 1550, 1520 cm$^{-1}$.

N.M.R. $\delta$(DMSO-d$_6$, ppm): 3.67 (2H, d, J=4 Hz), 4.63 (1.5H, s), 4.88 (0.5H, s), 5.18 (1H, d, J=5 Hz), 5.45 (2H, s), 5.93 (1H, dd, J=5 Hz, 8 Hz), 6.72 (1H, t, J=4 Hz), 7.73 (2H, d, J=9 Hz), 8.28 (2H, d, J=9 Hz), 9.38 (1H, d, J=8 Hz), 11.27 (1H, s).

EXAMPLE I (i) Ethyl 4 chloro-3-oxo-2-n-propoxyiminovalerate (180.0 g.) was added to a stirred solution of 2-mercaptoethanol (71.6 g.) in chloroform (1.8 l.), and then a solution of triethylamine (93.1 g.) in chloroform (200 ml.) was added to the solution over 5 minutes. The solution was stirred at 20° C. for 80 minutes.

After washing the resultant mixture with 10% hydrochloric acid twice, a saturated aqueous solution of sodium bicarbonate twice and water in turn, the solution was dried over magnesium sulfate and concerntrated in vacuo to give ethyl 4-(2-hydroxyethylthio)-3-oxo-2-n-propoxyiminovalerate (178.7 g.).

I.R. $\nu_{max}^{Film}$: 2980, 1740, 1685 cm$^{-1}$.

N.M.R. $\delta$(CDCl$_3$, ppm): 0.99 (3H, t, J=8.0 Hz), 1.39 (3H, t, J=7.0 Hz), 1.50~2.10 (2H, m), 2.80 (2H, t, J=6.0 Hz), 3.74 (2H, s), 4.31 (2H, t, J=8.0 Hz), 4.34 (2H, q, J=7.0 Hz).

(ii) A solution of ethyl 4-(2-hydroxyethylthio)-3-oxo-2-n-propoxyiminoacetate (178.0 g.) and p-toluenesulfonic acid (25.0 g.) in toluene (1.6 l.) was stirred at 150° C. for 30 minutes while removing the produced water. After treating the resultant solution with activated charcoal, ethyl acetate (1 l.) was added to the solution. The solution was washed with a saturated aqueous solution of sodium bicarbonate twice and water twice, dried over magnesium sulfate, and then concentrated in vacuo to give ethyl 2-(2,3-dihydro-1,4-oxathiin-6-yl)-2-n-propoxyiminoacetate (mixture of syn isomer and anti siomer, 153.4 g.).

I.R. $\nu_{max}^{Film}$: 2970, 2940, 2880, 1735, 1665 cm$^{-1}$.

N.M.R. δ(CDCl$_3$, ppm): 0.92 (3H, t, J=7.0 Hz), 1.35 (3H, t, J=7.8 Hz), 1.27~1.9(2H, m), 3.06 (2H, m), 4.0~4.6 (6H, m), 5.67, 6.49 (1H, s,s).

(iii) Ethyl 2-(2,3-dihydro-1,4-oxathiin-6-yl)-2-n-propoxyiminoacetate (mixture of syn isomer and anti isomer, 1 g.) was added to a mixture of methanol (10 ml.) and 1 N aqueous solution of sodium hydroxide (6 ml.), and stirred at room temperature for 18 hours. After distilling off the methanol from the resultant solution in vacuo, a saturated aqueous solution of sodium bicarbonate (15 ml.) and ethyl acetate (15 ml.) were added to the residue and shaken sufficiently. The aqueous layer was separated, adjusted to pH 1.0 with 10% hydrochloric acid and extracted with ethyl acetate (20 ml.). The extract was washed with water, dried over magnesium sulfate and concentrated in vacuo. The residue was triturated with a mixture of n-hexane and diethyl ether (1:1). The precipitates were collected by filtration and washed with the same mixture to give 2-(2,3-dihydro-1,4-oxathiin-6-yl)-2-n-propoxyiminoacetic acid (syn isomer, 0.30 g.).

I.R. $\nu_{max}^{Film}$: 1740 cm$^{-1}$.

N.M.R. δ(DMSO-d$_6$, ppm): 0.86 (3H, t, J=7.5 Hz), 1.59 (2H, m), 3.07 (2H, t, J=4.0 Hz), 3.98 (2H, t, J=7.0 Hz), 4.28 (2H, t, J=4.0 Hz), 5.80 (1H, s).

EXAMPLE J (i) Ethyl 4-chloro-3-oxo-2-n-hexyloxyiminovalerate (255.0 g.), 2-mercaptoethanol (86.1 g.), triethylamine (11.13 g.) and chloroform (2.8 l.) were treated in a similar manner to that of Example I-(i) and stirred at room temperature for 3.5 hours. The resultant solution was treated in a similar manner to that of Example I-(i) to give ethyl 4-(2-hydroxyethylthio)-3-oxo-2-n-hexyloxyiminovalerate (290.5 g.).

I.R. $\nu_{max}^{Film}$: 2930, 1740, 1680 cm$^{-1}$.

N.M.R. δ(CDCl$_3$, ppm): 0.70~2.07 (14H, m), 2.53~3.07 (4H, m), 3.70 (2H, m), 4.22 (2H, t, J=8 Hz), 4.38 (2H, q, J=7 Hz).

(ii) Ethyl 4-(2-hydroxyethylthio)-3-oxo-2-n-hexyloxyiminovalerate (300 g.), p-toluenesulfonic acid (42.0 g.) and toluene (2.5 l.) were treated in a similar manner to that of Example I-(ii) and refluxed under heating for 1.5 hours. The resultant solution was treated in a similar manner to that of Example I-(ii) to give ethyl 2-(2,3-dihydro-1,4-oxathiin-6-yl)-2-n-hexyloxyiminoacetate (mixture of syn isomer and anti isomer, 186.8 g.).

I.R. $\nu_{max}^{Film}$: 2930, 1735, 1665 cm$^{-1}$.

N.M.R. δ(CDCl$_3$, ppm): 0.67~2.00 (14H, m), 3.10 (2H, m), 3.93~4.63 (6H, m), 5.63, 6.47 (1H, s,s,).

(iii) Ethyl 2-(2,3-dihydro-1,4-oxathiin-6-yl)-2-n-hexyloxyiminoacetate (mixture of syn isomer and anti isomer, 186.8 g.), 1 N aqueous solution of sodium hydroxide (472 ml.) and methanol (1.8 l.) were stirred at room temperature for 35 minutes and the insoluble substance was removed by filtration. The filtrate was stirred at room temperature for 43 hours and treated in a similar manner to that of Example I-(iii) to give 2-(2,3-dihydro-1,4-oxathiin-6-yl)-2-n-hexyloxyiminoacetic acid (syn isomer, 43 g.).

I.R. $\nu_{max}^{Nujol}$: 1735 cm$^{-1}$.

N.M.R. δ(DMSO-d$_6$, ppm): 0.67~2.13 (11H, m), 3.10 (2H, m), 4.00~4.60 (4H, m), 5.80 (1H, s).

EXAMPLE K (i) A solution of ethyl 4-bromo-2-hydroxyimino-3-oxovalerate (50 g.) in chloroform (100 ml) was added dropwise to a stirred solution of 2-mercaptoethanol (20.5 g.) and triethylamine (26.6 g.) in chloroform (100 ml) at room temperature over 1.5 hours, and stirred at the same temperature for 2 hours. After removing chloroform from the resultant solution in vacuo, water (600 ml) and ethyl acetate (600 ml) were added to the residue and adjusted to pH 1.0 with conc.hydrochloric acid. The ethyl acetate layer was separated, washed with water (200 ml), dried over magnesium sulfate and then concentrated in vacuo to give ethyl 4-(2-hydroxyethylthio)-2-hydroxyimino-3-oxovalerate (38.8 g.).

I.R. $\nu_{max}^{Film}$: 3450, 2980, 2930, 1730 cm$^{-1}$.

N.M.R. δ(CDCl$_3$, ppm): 1.37 (3H, t), 2.83 (2H, m), 3.67~4.0 (4H, m), 4.42 (2H, q).

(ii) Potassium iodide (3.98 g.) was added to a solution of allylbromide (2.90 g.) in acetone (45 ml,) and stirred at room temperature for an hour, and then the insoluble substance was removed by filtration.

The filtrate was added to a suspension of ethyl 4-(2-hydroxyethylthio)-2-hydroxyimino-3-oxovalerate (4.70 g.) and potassium carbonate (4.15 g) in acetone (40 ml.) and stirred at room temperature for 2 hours. The insoluble substance was removed by filtration, and the filtrate was concentrated in vacuo.

After adding diethyl ether (35 ml.) and water (50 ml.) to the residue, the mixture was shaken sufficiently. The organic layer was separated, washed with water (20 ml), dried over magnesium sulfate and concentrated in vacuo to give oily ethyl 2-allyloxyimino-4-(2-hydroxyethylthio)-3-oxovalerate (4.30 g.).

I.R. $\nu_{max}^{Film}$: 3460, 2980, 2930, 2860, 1730, 1680 cm$^{-1}$.

N.M.R. δ(CDCl$_3$, ppm): 1.36 (3H, t), 2.76 (2H, m), 3.68 (2H, m), 4.10~4.67 (4H, m), 4.75 (2H, m), 5.32 (2H, m), 5.96 (1H, m).

(iii) p-Toluenesulfonic acid (0.40 g.) was added to a solution of ethyl 2-allyloxyimino-4-(2-hydroxyethylthio)-3-oxovalerate (4.30 g.) in toluene (43 ml.), and refluxed under heating for 20 minutes while removing the produced water. After cooling, ethyl acetate (10 ml.) was added to the resultant solution and washed with water (40 ml.) twice. The solution was dried over magnesium sulfate and concentrated in vacuo to give oily residue (3.3 g.). The residue was subjected to column chromatography on silica gel and eluted with chloroform. The eluate was concentrated in vacuo to give ethyl 2-(2,3-dihydro-1,4-oxathiin-6-yl)-2-allyloxyiminoacetate (2.92 g.).

I.R. $\nu_{max}^{Film}$: 3060, 2980, 2940, 2880, 1730 cm$^{-1}$

N.M.R. δ(CDCl$_3$, ppm): 1.33 (3H, t), 3.07 (2H, m), 4.17~4.50 (4H, m), 4.67 (2H, m), 5.30 (2H, m), 5.67 (1H, s), 6.60 (1H, m).

(iv) 1 N Aqueous solution of sodium hydroxide (1.22 ml.) was added to a solution of ethyl 2-(2,3-dihydro-1,4-oxathiin-6-yl)-2-allyloxyiminoacetate (0.90 g.) in methanol (9 ml.) and stirred at room temperature for 22 hours. After removing methanol from the solution, the residue was dissolved in water (20 ml.). The solution was adjusted to pH 7.0 with conc.hydrochloric acid, washed with ethyl acetate (20 ml.), adjusted to pH 1.5 with conc.hydrochloric acid and extracted with ethyl acetate (50 ml.). The extract was washed with water (50 ml.), dried over magnesium sulfate and concentrated in vacuo. The residue was recrystallized from a mixture of diisopropyl ether, diethyl ether and n-hexane (1:1:1) to give 2-(2,3-dihydro-1,4-oxathiin-6-yl)-2-allyloxyiminoacetic acid (syn isomer, 0.50 g.), colorless crystals, mp 119° to 121° C.

I.R. $\nu_{max}^{Nujol}$: 3060, 1730 cm$^{-1}$.

N.M.R. δ(CDCl₃, ppm): 3.05 (2H, m), 4.40 (2H, m), 4.68 (2H, m), 5.30 (2H, m), 5.83 (1H, s), 6.02 (1H, m).

EXAMPLE 1

7-[2-(2,3-Dihydro-1,4-oxothiin-6-yl)-2-methoxyiminoacetamido]cephalosporanic acid (syn isomer)

Phosphoryl chloride (820 mg.) was added to a solution of dry N,N-dimethylformamide (400 mg.) in dry ethyl acetate (1.5 ml.) at 5° C. over 10 minutes, and stirred at 5° to 10° C. for 30 minutes to prepare a Vilsmeier reagent. To the solution were added all at once 2-(2,3-dihdyro-1,4-oxathiin-6-yl)-2-methoxyiminoacetic acid (syn isomer, 1 g.) and dry ethyl acetate (8 ml.) at −10° C., and the mixture was stirred at −5° C. for 30 minutes to give the acid chloride solution. On the other hand, a mixture of 7-aminocephalosporanic acid (1.4 g.), trimethylsilylacetamide (5.4 g.) and dry ethyl acetate (50 ml.) was stirred to give a solution. The above acid chloride solution was added all at once to the solution at −15° C., and stirred at −10° C. for 2 hours. Water (30 ml.) was added to the resultant solution and shaken sufficiently, and then the organic layer was separated. After water (30 ml.) was added to the organic layer, the solution was adjusted to pH 6.5 with sodium bicarbonate, and the aqueous layer was separated. The aqueous layer was washed with methylene chloride and the organic solvent was removed by introducing nitrogen gas. The solution was adjusted to pH 2.0 with 10% hydrochloric acid under ice-cooling, and the precipitates were collected by filtration, washed with water and dried to give 7-[2-(2,3-dihydro-1,4-oxathiin-6-yl)-2-methoxyiminoacetamido]cephalosporanic acid (syn isomer, 1.7 g.), pale yellow powder, mp 175° to 177° C. (dec.).

I.R. $\nu_{max}^{Nujol}$: 3300, 2500~2600, 1775, 1740, 1720, 1645 cm⁻¹.

N.M.R. δ(DMSO-d₆, ppm): 2.10 (3H, s), 3.10 (2H, broad s), 3.55 (2H, AR-q, J=18 Hz), 3.85 (3H, s), 4.20 (2H, broad s), 4.85 (2H, AB-q, J=13 Hz), 5.15 (1H, d, J=5 Hz), 5.65~5.75 (2H, m), 9.60 (1H, d, J=8 Hz).

EXAMPLE 2

7-[2-(2,3-Dihydro-1,4-oxathiin-6-yl)-2-methoxyiminoacetamido]-3-carbamoyloxymethyl-3-cephem-4-carboxylic acid (syn isomer)

2-(2,3-Dihydro-1,4-oxathiin-6-yl)-2-methoxyiminoacetic acid (syn isomer, 0.508 g.) was allowed to react with 7-amino-3-carbamoyloxymethyl-3-cephem-4-carboxylic acid (0.82 g.) in a similar manner to that of Example 1 to give the captioned compound (0.85 g.), pale yellow powder, mp. 175° to 180° C. (dec.).

I.R. $\nu_{max}^{Nujol}$: 3450, 3350, 3300, 2600, 1765, 1720, 1660 cm⁻¹.

N.M.R. δ(DMSO-d₆, ppm): 3.06 (2H, broad s), 3.62 (2H, AB-q, J=18 Hz), 3.80 (3H, s), 4.26 (2H, broad s), 4.76 (2H, AB-q, J=13 Hz), 5.13 (1H, d, J=5 Hz), 5.68 (1H, dd, J=5 Hz, 8 Hz), 5.76 (1H, s), 6.56 (2H, s), 9.60 (1H, d, J=8 Hz).

EXAMPLE 3

7-[2-(2,3-Dihydro-1,4-oxathiin-6-yl)-2-methoxyiminoacetamido]-3-(1,3,4-thiadiazol-2-yl)thiomethyl-3-cephem-4-carboxylic acid (syn isomer)

2-(2,3-Dihydro-1,4-oxathiin-6-yl)-2-methoxyiminoacetic acid (syn isomer, 1 g.) was allowed to react with 7-amino-3-(1,3,4-thiadiazol-2-yl)thiomethyl-3-cephem-4-carboxylic aid (1.8 g.) in a similar manner to that of Example I to give the captioned compound (2.3 g.), pale yellow powder, mp. 160° to 165° C. (dec.).

I.R. $\nu_{max}^{Nujol}$: 3300, 2600, 1785, 1730, 1670 cm⁻¹.

N.M.R. δ(DMSO-d₆, ppm): 3.10 (2H, broad s), 3.78 (2H, AB-q, J=18 Hz), 3.82 (3H, s), 4.15 (2H, broad s), 4.48 (2H, AB-q, J=13 Hz), 5.17 (1H, d, J=5 Hz), 5.65~5.76 (2H, m), 9.53 (1H, s), 9.65 (1H, d, J=8 Hz).

EXAMPLE 4

7-[2-(2,3-Dihydro-1,4-oxathiin-6-yl)-2-methoxyiminoacetamido]-3-(5-methyl-1,3,4-thiadiazol-2-yl)thiomethyl-3-cephem-4-carboxylic acid (syn isomer)

2-(2,3-Dihydro-1,4-oxathiin-6-yl)-2-methoxyiminoacetic acid (syn isomer, 1 g.) was allowed to react with 7-amino-3-(5-methyl-1,3,4-thiadiazol-2-yl)thiomethyl-3-cephem-4-carboxylic acid (2 g.) in a similar manner to that of Example 1 to give the captioned compound (2.2 g.), pale yellow powder, mp. 160° to 165° C. (dec.).

I.R. $\nu_{max}^{Nujol}$: 3300, 2500~2600, 1780, 1720, 1675, 1620 cm⁻¹.

N.M.R. δ(DMSO-d₆, ppm): 2.70 (3H, s), 3.05 (2H, broad s), 3.70 (2H, AB-q, J=18 Hz), 3.85 (3H, s), 4.21 (2H, broad s), 4.30 (2H, AB-q, J=13 Hz), 5.15 (1H, d, J=5 Hz), 5.68 (1H, dd, J=5 Hz, 8 Hz), 5.75 (1H, s), 9.68 (1H, d, J=8 Hz).

EXAMPLE 5

7-[2-(2,3-Dihydro-1,4-oxathiin-6-yl)-2-methoxyiminoacetamido]-3-(1-methyl-1H-tetrazol-5-yl)-thiomethyl-3-cephem-4-carboxylic acid (syn isomer)

2-(2,3-Dihydro-1,4-oxathiin-6-yl)-2-methoxyiminoacetic acid (syn isomer, 1 g.) was allowed to react with 7-amino-3-(1-methyl-1H-tetrazol-5-yl)thiomethyl-3-cephem-4-carboxylic acid (2 g.) in a similar manner to that of Example I to give the captioned compound (2.0 g.), pale yellow powder, mp. 145° to 150° C. (dec.).

I.R. $\nu_{max}^{Nujol}$: 3300, 2600~2550, 1785, 1730, 1680 cm⁻¹.

N.M.R. δ(DMSO-d₆, ppm): 3.04 (2H, broad s), 3.68 (2H, AB-q, J=18 Hz), 3.76 (3H, s), 3.90 (3H, s), 4.28 (4H, m), 5.06 (1H, d, J=4 Hz), 5.6~5.75 (2H, m), 9.56 (1H, d, J=8 Hz).

EXAMPLE 6

7-[2-(2,3-Dihydro-1,4-oxathiin-6-yl)-2-methoxyiminoacetamido]-3-(1-methyl-1H-tetrazol-5-yl)-thiomethyl-3-cephem-4-carboxylic acid (anti isomer)

2-(2,3-Dihydro-1,4-oxathiin-6-yl)-2-methoxyiminoacetic acid (anti isomer, 1 g.) was allowed to react with 7-amino-3-(1-methyl-1H-tetrazol-5-yl)thiomethyl-3-cephem-4-carboxylic acid (2 g.) in a similar manner to that of Example 1 to give the captioned compound (1.8 g.), pale yellow powder, mp 144° to 148° C. (dec.).

I.R. $\nu_{max}^{Nujol}$: 3300, 2600, 1780, 1720, 1675, 1625 cm⁻¹.

N.M.R. δ(DMSO-d₆, ppm) 3.06 (2H, broad s), 3.70 (2H, AB-q, J=18 Hz); 3.00 (3H, s), 3.96 (3H, s), 4.20 (2H, broad s), 4.32 (2H, AB-q, J=13 Hz), 5.10 (1H, d, J=5 Hz), 5.80 (1H, dd, J=5 Hz, 8 Hz), 6.72 (1H, s), 9.28 (1H, d, J=8 Hz).

EXAMPLE 7

7-[2-(2,3-Dihydro-1,4-dithiin-5-yl)-2-methox-yiminoacetamido]-3-(1,3-4-thiadiazol-2-yl)-thiomethyl-3-cephem-4-carboxylic acid (syn isomer)

2-(2,3-Dihydro-1,4-dithiin-5-yl)-2-methoxyiminoacetic acid (syn isomer, 1.1 g.) was allowed to react with 7-amino-3-(1,3,4-thiadiazol-2-yl)thiomethyl-3-cephem-4-carboxylic acid (1.7 g.) in a similar manner to that of Example 1 to give the captioned compound (2 g.), pale yellow powder, mp. 192° to 194° C. (dec.).

I.R. $\nu_{max}^{Nujol}$: 3300, 2600~2550, 1780, 1725, 1675 cm$^{-1}$.

N.M.R. $\delta$ (DMSO-d$_6$, ppm): 3.22 (4H, broad s), 3.65 (2H, AB-q, J=18 Hz), 3.84 (3H, s), 4.48 (2H, AB-q, J=13 Hz), 5.16 (1H, d, J=5 Hz), 5.76 (1H, d, d, J=5 Hz, 8 Hz), 6.62 (1H, s), 9.56 (1H, s), 9.76 (1H, d, J=8 Hz).

EXAMPLE 8

7-[2-(4-Formyl-2,3-dihydro-4H-1,4-thiazin-5-yl)-2-methoxyiminoacetamido]-3-(1-methyl-1H-tetrazol-5-yl)thiomethyl-3-cephem-4-carboxylic acid (syn isomer)

2-(4-Formyl-(2,3-dihydro-4H-1,4-thiazin-5-yl)-2-methoxyiminoacetic acid (syn isomer, 2.3 g.) was allowed to react with 7-amino-3-(1-methyl-1H-tetrazol-5-yl)thiomethyl-3-cephem-4-carboxylic acid (3.3 g.) in a similar manner to that of Example 1 to give the captioned compound (2.5 g.), pale yellow powder, mp. 150° to 155° C. (dec.).

I.R. $\nu_{max}^{Nujol}$: 3300, 2600~2550, 1785, 1725, 1690, 1675 cm$^{-1}$.

N.M.R. $\delta$ (DMSO-d$_6$, ppm): 3.10 (2H, broad s), 3.70 (2H, AB-q, J=18 Hz), 3.78 (3H, s), 3.85 (2H, broad s), 3.90 (3H, s), 4.30 (2H, AB-q, J=13 Hz), 5.10 (1H, d, J=5 Hz), 5.70 (1H, d,d, J=5 Hz, 8 Hz), 6.25 (1H, s), 8.50 (1H, s), 9.63 (1H, d, J=8 Hz).

EXAMPLE 9

7-[2-(2-Oxo-1,3-dithiol-4-yl)-2-methox-yiminoacetamido]-3-(1,3,4-thiadiazol-2-yl)thiomethyl-3-cephem-4-carboxylic acid (syn isomer)

2-(2-Oxo-1,3-dithiol-4-yl)-2-methoxyiminoacetic acid (syn isomer, 0.2 g.) was allowed to react with 7-amino-3-(1,3,4-thiadiazol-2-yl)thiomethyl-3-cephem-4-carboxylic acid (1.2 g.) in a similar manner to that of Example 1 and crystallized with diisoporpyl ether to give the captioned compound (0.15 g.), mp. 80° to 90° C. (dec.).

I.R. $\nu_{max}^{Nujol}$: 1780, 1710, 1640 cm$^{-1}$.

N.M.R. $\delta$ (acetone-d$_6$, ppm): 3.85 (2H, broad s), 3.98 (3H, s), 4.59 (2H, AB-q, J=14 Hz), 5.29 (1H, d, J=5 Hz), 5.97 (1H, d, J=5 Hz), 7.45 (1H, s), 9.42 (1H, s).

EXAMPLE 10

7-[2-(2-Oxo-1,3-dithiol-4-yl)-2-methox-yiminoacetamido]-3-(1,3,4-thiadiazol-2-yl)thiomethyl-3-cephem-4-carboxylic acid (anti isomer)

2-(2-Oxo-1,3-dithiol-4-yl)-2-methoxyiminoacetic acid (anti isomer, 0.7 g.) was allowed to react with 7-amino-3-(1,3,4-thiadiazol-2-yl)thiomethyl-3-cephem-4-carboxylic acid (1.06 g.) in a similar manner to that of Example 1 to give the captioned compound (0.85 g.).

I.R. $\nu_{max}^{Nujol}$: 1780, 1710, 1670, 1640 cm$^{-1}$.

N.M.R. $\delta$ (DMSO-d$_6$, ppm): 3.72 (2H, broad s), 4.05 (3H, s), 4.46 (2H, AB-q, J=14 Hz), 5.17 (1H, d, J=6 Hz), 5.72 (1H, dd, J=8 Hz, 6 Hz), 7.98 (1H, s), 9.50 (1H, d, J=8 Hz), 9.52 (1H, s).

EXAMPLE 11

7-[2-(1,4-Benzoxathiin-2-yl)-2-methox-yiminoacetamido]-3-(1,3,4-thiadiazol-2-yl)thiomethyl-3-cephem-4-carboxylic acid (syn isomer)

2-(1,4-Benzoxathiin-2-yl)-2-methoxyiminoacetic acid (syn isomer, 0.85 g.) was allowed to react with 7-amino-3-(1,3,4-thiadiazol-2-yl)thiomethyl-3-cephem-4-carboxylic acid (1.09 g.) in a similar manner to that of Example 1 to give the captioned compound (1.50 g.), yellow powder, mp. 157° to 161° C. (dec.).

I.R. $\nu_{max}^{Nujol}$: 3350, 2600~2500, 1780, 1720, 1670, 1625 cm$^{-1}$.

N.M.R. $\delta$ (DMSO-d$_6$, ppm): 3.75 (2H, AB-q, J=18 Hz), 3.90 (3H, s), 4.55 (2H, AB-q, J=13 Hz), 5.17 (1H, d, J=5 Hz), 5.80 (1H, dd, J=5 Hz, 8 Hz), 6.05 (1H, s), 6.8~7.15 (4H, m), 9.60 (1H, s), 9.78 (1H, d, J=8 Hz).

EXAMPLE 12

7-[2-(1,4-Benzodithiin-2-yl)-2-methox-yiminoacetamido]-3-(1,3,4-thiadiazol-2-yl)thiomethyl-3-cephem-4-carboxylic acid (syn isomer)

2-(1,4-Benzodithiin-2-yl)-2-methoxyiminoacetic acid (syn isomer, 0.75 g.) was allowed to react with 7-amino-3-(1,3,4-thiadiazol-2-yl)thiomethyl-3-cephem-4-carboxylic acid (1 g.) in a similar manner to that of Example 1 to give the captioned compound (0.7 g.), yellow powder, mp. 142° to 147° C. (dec.).

I.R. $\nu_{max}^{Nujol}$: 3300, 2600, 1775, 1720, 1665, 1620, 1600 cm$^{-1}$.

N.M.R. $\delta$ (DMSO-d$_6$, ppm): 3.68 (2H, AB-q, J=18 Hz), 3.90 (3H, s), 5.40 (2H, AB-q, J=13 Hz), 5.16 (1H, d, J=5 Hz), 5.80 (1H, dd, J=5 Hz, 8 Hz), 6.84 (1H, s), 7.2~7.4 (4H, m), 9.50 (1H, s), 9.76 (1H, d, J=8 Hz).

EXAMPLE 13

7-[2-(2,3-Dihydro-1,4-dithiin-5-yl)-2-methox-yiminoacetamido]-3-(1-methyl-1H-tetrazol-5yl)-thiomethyl-3-cephem-4-carboxylic acid (syn isomer)

2-(2,3-Dihydro-1,4-dithiin-5-yl)-2-methoxyiminoacetic acid (syn isomer, 1.2 g.) was allowed to react with 7-amino-3-(1-methyl-1H-tetrazol-5-yl)thiomethyl-3-cephem-4-carboxylic acid (1.65 g.) in a similar manner to that of Example 1 to give the captioned compound (2.1 g.), pale yellowish white powder.

I.R. $\nu_{max}^{Nujol}$: 3300, 2600~2500, 1790, 1730, 1680, 1630 cm$^{-1}$.

N.M.R. $\delta$ (DMSO-d$_6$, ppm): 3.25 (4H, s), 3.72 (2H, AB-q, J=18 Hz), 3.85 (3H, s), 3.95 (3H, s), 4.38 (2H, AB-q, J=13 Hz), 5.17 (1H, d, J=5 Hz), 5.78 (1H, dd, J=5 Hz, 8 Hz), 6.63 (1H, s), 9.77 (1H, d, J=9 Hz).

EXAMPLE 14

7-[2-(2,3-Dihydro-1,4-dithiin-5-yl)-2-methox-yiminoacetamido]-2-methyl-3-cephem-4-carboxylic acid (syn isomer)

The Vilsmeier reagent was prepared from dry N,N-dimethylformamide (0.44 g.), ethyl acetate (2 ml.) and phosphoryl chloride (0.92 g.) in conventional manner. Ethyl acetate (10 ml.) and 2-(2,3-dihydro-1,4-dithiin-5-yl)-2-methoxyiminoacetic acid (syn isomer, 1.2 g.) were added to the Vilsmeier reagent to give the acid chloride solution. On the other hand, 7-amino-2-methyl-3-cephem-4-carboxylic acid (1.07 g.), trimethylsilylacetamide (4.5 g.) and ethyl acetate (20 ml.) were mixed and stirred at room temperature for an hour. The solution was cooled at −15° C. and the acid chloride solution obtained above was added all at once thereto under stirring, and then the solution was stirred at −10° C. for an hour. After adding water (60 ml.) to the resultant solution, the organic layer was separated.

Water (150 ml.) was added to the organic layer, and then adjusted to pH 6.5 with sodium bicarbonate. The aqueous layer was separated, washed with diethyl ether, and the organic solvent was removed by introducing nitrogen gas. The aqueous solution was adjusted to pH 2.2 with 10% hydrochloric acid under ice-cooling. The precipitates were collected by filtration, washed with water and dried over magnesium sulfate to give 7-[2-(2,3-dihydro-1,4-dithiin-5-yl)-2-methoxyiminoacetamido]-2-methyl-3-cephem-4-carboxylic acid (syn isomer, 1.45 g.), pale yellow powder.

I.R. $\nu_{max}^{Nujol}$: 3300, 2500~2600, 1790, 1735, 1670, 1635 cm$^{-1}$.

N.M.R. δ (DMSO-d$_6$, ppm): 1.43 (3H, d, J=7 Hz), 3.18 (4H, s), 3.7 3.8 (4H, m), 5.10 (1H, d, J=5 Hz), 5.79 (1H, dd, J=5 Hz, 8 Hz), 6.50 (1H, d, J=6 Hz), 6.55 (1H, s), 9.65 (1H, d, J=8 Hz).

EXAMPLE 15

7-[2-(2,3-Dihydro-1,4-dithiin-5-yl)-2-methoxyiminoacetamido]-3-cephem-4-carboxylic acid (syn isomer)

(i) The Vilsmeier reagent was prepared from dry N,N-dimethylformamide (440 mg.), dry ethyl acetate (2.0 ml.) and phosphoryl chloride (920 mg.) in conventional manner. Dry ethyl acetate (10 ml.) and 2-(2,3-dihydro-1,4-dithiin-5-yl)-2-methoxyiminoacetic acid (syn isomer, 1.2 g.) were added to the Vilsmeier reagent to prepare an acid chloride solution. On the other hand, 4-nitrobenzyl 7-amino-3-cephem-4-carboxylic acid (1.68 g.), trimethylsilylacetamide (4.6 mg.) and dry ethyl acetate (20 ml.) were mixed and stirred at 40° to 50° C. for 1.5 hours. After the solution was chilled at −15° C., the acid chloride solution obtained above was added all at once to the solution with stirring, and stirred at −10° C. for an hour. To the resultant solution was added water (60 ml.), and the solution was stirred below 10° C. for 1.5 hours. The precipitates were collected by filtration, washed with water, and dried to give 4-nitrobenzyl 7-[2-(2,3-dihydro-1,4-dithiin-5-yl)-2-methoxyiminoacetamido]-3-cephem-4-carboxylate (syn isomer, 2.1 g.), yellow powder.

I.R. $\nu_{max}^{Nujol}$: 3350, 1785, 1700, 1690, 1635, 1610, 1530, 1350 cm$^{-1}$.

N.M.R. δ (DMSO-d$_6$, ppm): 3.20 (4H, s), 3.53 (2H, d, J=4 Hz), 3.90 (3H, s), 5.16 (1H, d, J=5 Hz), 5.35 (2H, s), 5.68 (1H, dd, J=5 Hz, 8 Hz), 6.48 (1H, s), 6.58 (1H, d, J=5 Hz), 7.58 (2H, d, J=9 Hz), 8.23 (2H, d, J=9 Hz), 9.60 (1H, d, J=8 Hz).

(ii) Palladium carbon (0.8 g.) was added to a mixture of 4-nitrobenzyl 7-[2-(2,3-dihydro-1,4-dithiin-5-yl)-2-methoxyiminoacetamido]-3-cephem-4-carboxylate (syn isomer, 2.0 g.), methanol (20 ml.), tetrahydrofuran (40 ml.), acetic acid (0.3 ml.) and water (3 ml.), and subjected to catalytic reduction under ordinary pressure at room temperature for 4 hours. After removing the catalyst from the resultant mixture by filtration, the filtrate was concentrated at 40° C. in vacuo. Ethyl acetate (20 ml.) was added to the residue, and the solution was adjusted to pH 6.5 to 7.0 with a saturated aqueous solution of sodium bicarbonate, stirred for 30 minutes and then filtered. The insoluble product was washed with water (10 ml.). The filtrate and washings were combined together, and the aqueous layer was separated washed with ethyl acetate and adjusted to pH 5.0 with 10% hydrochloric acid. The solution was treated with activated charcoal (0.1 g.) for 5 minutes and then filtered in vacuo. The filtrate was washed with diethyl ether and the organic solvent was removed by introducing nitrogen gas. The aqueous layer was adjusted to pH 2.0 with 10% hydrochloric acid under ice cooling and extracted with ethyl acetate (50 ml.) twice. The extract was washed with ice-water, dried over magnesium sulfate and filtered. The filtrate was concentrated at 40° C. in vacuo and the residue was crystallized with diethyl ether (30 ml.). The crystals were collected by filtration, washed with diethyl ether and dried to give 7-[2-(2,3-dihydro-1,4-dithiin-5-yl)-2-methoxyiminoacetamido]-3-cephem-4-carboxylic acid (syn isomer, 0.9 g.), pale yellow powder.

I.R. $\nu_{max}^{Nujol}$: 3300, 2500~2600, 1790, 1735, 1660, 1610 cm$^{-1}$.

N.M.R. δ (DMSO-d$_6$, ppm): 3.16 (4H, s), 3.58 (2H, d, J=4 Hz), 3.77 (3H, s), 5.09 (1H, d, J=5 Hz), 5.78 (1H, dd, J=5 Hz, 8 Hz), 6.43 (1H, d, J=5 Hz), 6.54 (1H, s), 9.60 (1H, d, J=8 Hz).

EXAMPLE 16

7-[2-(2,3-dihydro-4H-1,4-thiazin-5-yl)-2-hydroxyiminoacetamido]-3-cephem-4-carboxylic acid (syn isomer)

(i) A suspension of 2-aminoethanethiol hydrochloride (0.25 g.) in water (1 ml.) and tetrahydrofuran (2 ml.) was adjusted, to pH 7.5 with a saturated aqueous solution of sodium bicarbonate. The solution was added to a suspension of 4-nitrobenzyl 7-(2-hydroxyimino-3-oxo-4-bromobutyramido)-3-cephem-4-carboxylate (syn isomer, 1.05 g.) in tetrahydrofuran (30 ml.) and stirred at room temperature for 4 hours. The resultant solution was concentrated in vacuo, and water and ethyl acetate were added to the residue. The ethyl acetate layer was separated, washed with a saturated aqueous solution of sodium chloride, dried over magnesium sulfate and then concentrated in vacuo. Diethyl ether was added to the residue and the precipitates were collected by filtration to give 4-nitrobenzyl 7-[2-(2,3-dihydro-4H-thiazin-5-yl)-2-hydroxyiminoacetamido]-3-cephem-4-carboxylate. (syn isomer, 0.5 g.).

I.R. $\nu_{max}^{Nujol}$: 3350~3200, 1780, 1730, 1670, 1630, 1605, 1520 cm$^{-1}$.

N.M.R. δ (DMSO-d$_6$, ppm): 2.93 (2H, m), 3.83~3.30 (4H, m), 5.03 (1H, s), 5.18 (1H, d, J=5 Hz), 5.47 (2H, broad s), 5.88 (1H, d, J=5 Hz), 6.70 (1H, t, J=5 Hz), 7.75 (1H, d, J=9 Hz), 8.30 (1H, d, J=9 Hz).

(ii) Thus obtained 4 nitrobenzyl 7-[2-(2,3-dihydro-4H-thiazin-5-yl)-2-hydroxyiminoacetamido]-3-cephem-4-carboxylate (syn isomer, 0.5 g.) was dissolved in a mixture of tetrahydrofuran (15 ml.) and methanol (15 ml.). 10% Palladium carbon (0.3 g.) was added to the solution, and subjected to catalytic reduction under ordinary pressure at room temperature. The catalyst was removed from the resultant mixture by filtration, and the filtrate was concentrated in vacuo. After water and ethyl acetate were added to the residue, the solution was adjusted to pH 8.0 with an aqueous solution of sodium bicarbonate. The insoluble substance was filtered out and the aqueous solution was separated. The aqueous solution was adjusted to pH 5.5 and washed with ethyl acetate and methylene chloride, and the organic solvent was removed by introducing nitrogen gas. The solution was adjusted to pH 3.3 and subjected to column chromatography on nonionic adsorption resin "Diaion HP-20" [Trademark: Manufactured by Mitsubishi Chemical Industries Ltd. (30 ml.)]. The column was washed with water and eluted with 40% aqueous acetone. The eluate was concentrated in vacuo and lyophilized to give 7-[2-(2,3-dihydro-4H-1,4-thiazin-5-yl)-2-hydroxyiminoacetamido]-3-cephem-4-carboxylic acid (syn isomer, 90 mg.).

I.R. $\nu_{max}^{Nujol}$: 3400~3200, 1750, 1650, 1590 cm$^{-1}$.

N.M.R. δ (DMSO-d$_6$, ppm): 2.90 (2H, m), 3.80~3.30 (4H, m), 5.00 (2H, m), 5.63 (1H, m), 6.3 (1H, m).

EXAMPLE 17

7-[2-(2,3-Dihydro-1,4-dithiin-5-yl)-2-methoxyiminoacetamido]-3-methyl-3-cephem-4-carboxylic acid (syn isomer)

2-(2,3-Dihydro-1,4-dithiin-5-yl)-2-methoxyiminoacetic acid (syn isomer, 1.15 g.) was allowed to react with 7-amino-3-methyl-3-cephem-4-carboxylic acid (1.07 g.) in a similar manner to that of Example 1 to give the captioned compound (0.8 g.), pale yellow powder.

I.R. $\nu_{max}^{Nujol}$: 3300, 2500~2600, 1785, 1720, 1660, 1640, 1620 cm$^{-1}$.

N.M.R. δ (DMSO-d$_6$, ppm): 2.00 (3H, s), 3.17 (4H, s), 3.43 (2H, AB-q, J=12 Hz), 3.75 (3H, s), 5.10 (1H, d, J=5 Hz), 5.65 (1H, dd, J=5 Hz, 8 Hz), 6.62 (1H, s), 9.70 (1H, d, J=8 Hz).

EXAMPLE 18

7-[2-(2,3-Dihydro-1,4-oxathiin-6-yl)-2-methoxyiminoacetamido]-3-cephem-4-carboxylic acid (syn isomer)

(i) The Vilsmeier reagent was prepared from dry N,N-dimethylformamide (1.25 g.), phosphoryl chloride (2.61 g.) and dry ethyl acetate (6 ml.) in conventional manner. Ethyl acetate (20 ml.) was added to the solution, and 2-(2,3-dihydro-1,4-oxathiin-6-yl)-2-methoxyiminoacetic acid (syn isomer, 3.0 g.) was added all at once to the solution at −10° C. and then stirred at the same temperature for 30 minutes to prepare an acid chloride solution. On the other hand, a mixture of 4-nitrobenzyl 7-amino-3-cephem-4-carboxylate (4.51 g.), trimethylsilylacetamide (14.2 g.) and ethyl acetate (180 ml.) was stirred at 45° C. for an hour. The acid chloride solution obtained above was added all at once to the solution at −15° C. and stirred at the same temperature for an hour. To the resultant solution was added water (100 ml.), and the organic layer was separated. The organic solution was washed with a saturated aqueous solution (60 ml.) of sodium bicarbonate and a saturated aqueous solution (100 ml.) of sodium chloride in turn, dried over magnesium sulfate, and concentrated in vacuo. The residue was washed with diethyl ether and the precipitates were collected by filtration to give 4-nitrobenzyl 7-[2-(2,3-dihydro-1,4-oxathiin-6-yl)-2-methoxyiminoacetamido]-3-cephem-4-carboxylate (syn isomer, 4.8 g.).

I.R. $\nu_{max}^{Nujol}$: 3280, 1770, 1730, 1650 cm$^{-1}$.

N.M.R. δ (DMSO-d$_6$, ppm): 3.08 (2H, broad s), 3.64 (2H, AB-q, J=18 Hz), 3.80 (3H, s), 4.27 (2H, broad s), 5.12 (1H, d, J=8 Hz), 5.40 (2H, s), 5.76 (1H, s), 5.80 (1H, dd, J=5 Hz, 8 Hz), 6.65 (1H, t, J=4 Hz), 7.70 (2H, d, J=9 Hz), 8.22 (2H, d, J=9 Hz), 9.40 (1H, d, J=8 Hz).

(ii) Thus obtained 4-nitrobenzyl 7-[2-(2,3-dihydro-1,4-oxathiin-6-yl)-2-methoxyiminoacetamido]-3-cephem-4-carboxylate (syn isomer, 3.30 g.) was suspended in a mixture of tetrahydrofuran (150 ml.), methanol (70 ml.), water (10 ml.) and acetic acid (1 ml.). 10% Palladium carbon (2.3 g.) was added to the solution, and subjected to catalytic reduction at room temperature for 45 minutes. After removing the catalyst from the resultant solution by filtration, the filtrate was concentrated in vacuo. Water and a saturated aqueous solution of sodium bicarbonate were added to the residue and adjusted to pH 7.0. After filtration, the filtrate was washed with ethyl acetate (60 ml.) and methylene chloride (20 ml.), and then the organic solvent was removed by introducing nitrogen gas. The solution was adjusted to pH 2.0 with 10% hydrochloric acid under ice cooling. The precipitates were collected by filtration, washed with water and dried to give 7-[2-(2,3-dihydro-1,4-oxathiin-6-yl)-2-methoxyiminoacetamido]-3-cephem-4-carboxylic acid (syn isomer, 1.55 g.).

I.R. $\nu_{max}^{Nujol}$: 3225, 1770, 1660 cm$^{-1}$.

N.M.R. δ(DMSO-d$_6$, ppm): 3.07 (2H, broads), 3.57 (2H, AB-q, J=18 Hz), 3.78 (3H, s), 4.27 (2H, broad s), 5.06 (1H, d, J=5 Hz), 5.71 (1H, s), 5.72 (1H, dd, J=5 Hz, 8 Hz), 6.45 (1H, t, J=4 Hz), 9.58 (1H, d, J=8 Hz).

EXAMPLE 19

7-[2-(2,3-Dihydro-1,4-oxathiin-6-yl)-2-methoxyiminoacetamido]-3-chloro-3-cephem-4-carboxylic acid (syn isomer)

(i) The Vilsmeier reagent was prepared from N,N-dimethylformamide (0.4 g.) and phosphoryl chloride (0.86 g.) in conventional manner, and suspended in dry ethyl acetate (20 ml.). 2-(2,3-Dihydro-1,4-oxathiin-6-yl)-2-methoxyiminoacetic acid (syn isomer, 1.0 g.) was added to the suspension at −5° C. and stirred at the same temperature for 30 minutes to prepare an acid chloride solution. On the other hand, 4-nitrobenzyl 7-amino-3-chloro-3-cephem-4-carboxylate hydrochloride (2.0 g.) was dissolved in a solution of trimethylsilylacetamide (5.2 g.) in ethyl acetate (40 ml.). The acid chloride solution obtained above was added to the solution at −30° C. and stirred at −20° to −10° C. for 2 hours. Water was added to the resultant solution at −20° C., and extracted with ethyl acetate (160 ml.). The extract was washed with a saturated aqueous solution of sodium bicarbonate and a saturated aqueous solution of sodium chloride in turn, dried over magnesium sulfate and then concentrated in vacuo. The residue was triturated with diisopropyl ether, and the precipitates were collected by filtration and dried to give 4-nitrobenzyl 7-[2-(2,3-dihydro-1,4-oxathiin-6-yl)-2-methoxyiminoacetamido]-3-chloro-3-cephem-4-carboxylate (syn isomer, 2.6 g.).

I.R. $\nu_{max}^{Nujol}$: 3250, 1775, 1730, 1655, 1610, 1590, 1525 cm$^{-1}$.

N.M.R. δ(DMSO-d$_6$, ppm): 3.10 (2H, broad s), 3.83 (3H, s), 3.93 (2H, broad s), 4.28 (2H, broad s), 5.32 (1H, d, J=5 Hz), 5.48 (2H, s), 5.75 (1H, s), 5.85 (1H, dd, J=5 Hz, 8 Hz), 7.73 (1H, d, J=9 Hz), 8.27 (1H, d, J=9 Hz), 9.73 (1H, d, J=8 Hz).

(ii) Thus obtained 4-nitrobenzyl 7-[2-(2,3-dihydro-1,4-oxathiin-6-yl)-2-methoxyiminoacetamido]-3-chloro-3-cephem-4-carboxylate (syn isomer, 2.5 g.) was dissolved in a mixture of tetrahydrofuran (40 ml.) and methanol (40 ml.). 10% Palladium carbon (1.2 g.) was added to the solution, and subjected to catalytic reduction under ordinary pressure at room temperature for 4 hours. After removing the catalyst from the resultant solution by filtration, the filtrate was concentrated in vacuo. Water and ethyl acetate were added to the residue and adjusted to pH 7.5 with a saturated aqueous solution of sodium bicarbonate. The insoluble substance was removed by filtration, and the aqueous solution was separated. After ethyl acetate was added to the aqueous solution, the solution was adjusted to pH 1.5 with 10% hydrochloric acid and extracted with ethyl acetate. The extract was washed with a saturated aqueous solution of sodium chloride, dried over magnesium sulfate, and then concentrated in vacuo. The residue was triturated with diisopropyl ether and the precipitates were collected by filtration to give 7-[2-(2,3-dihydro-1,4-oxathiin-6-yl)-2-methoxyiminoacetamido]-3-chloro-3-cephem-4-carboxylic acid (syn isomer, 1.3 g.).

I.R. $\nu_{max}{}^{Nujol}$: 3260, 1760, 1720, 1655, 1620, 1580, 1530 cm$^{-1}$.

N.M.R. $\delta$(DMSO-d$_6$, ppm): 3.10 (2H, broad s), 3.85 (3H, s), 3.87 (2H, broad s), 4.33 (2H, broad s), 5.27 (1H, d, J=5 Hz), 5.77 (1H, s), 5.78 (1H, dd, J=5 Hz, 8 Hz), 9.7 (1H, d, J=8 Hz).

EXAMPLE 20

7-[2-(2,3-Dihydro-1,4-oxathiin-6-yl)-2-methoxyiminoacetamido]-3-(1,3,4-thiadiazol-2-yl)thiomethyl-3-cephem-4-carboxylic acid (syn isomer)

7-[2-(2,3-Dihydro-1,4-oxathiin-6-yl)-2-methoxyiminoacetamido]cephalosporanic acid (syn isomer, 2.29 g.) and sodium bicarbonate (0.84 g.) were dissolved in a mixture of acetone (30 ml.) and water (38 ml.). 1,3,4-Thiadiazol-2-thiol (0.65 g.) was added to the solution, and stirred at 60° to 65° C. for 4 hours while keeping pH 6.5 to 7.5 with a saturated aqueous solution of sodium bicarbonate. The resultant solution was concentrated in vacuo, and water was added to the residue under cooling. The solution was adjusted to pH 2 with 10% hydrochloric acid and extracted with ethyl acetate. Water was added to the extract and adjusted to pH 6.5 with a saturated aqueous solution of sodium bicarbonate. The aqueous layer was separated, washed with methylene chloride, and the organic solvent was removed by introducing nitrogen gas. The solution was adjusted to pH 2 with 10% hydrochloric acid, and the precipitates were collected by filtration, washed with water and dried to give 7-[2-(2,3-dihydro-1,4-oxathiin-6-yl)-2-methoxyiminoacetamido]-3-(1,3,4-thiadiazol-2-yl)thiomethyl-3-cephem-4-carboxylic acid (syn isomer, 0.88 g.). The I.R. spectrum and N.M.R. spectrum of the compound was identical with those of the object compound obtained in Example 3.

EXAMPLE 21

Phosphoryl chloride (0.92 g.) was added to a stirred solution of N,N-dimethylformamide (0.44 g.) in ethyl acetate (2 ml.) at −5° to 10° C. over 2 minutes. Ethyl acetate (20 ml.) and 2-(2,3-dihydro-1,4-oxathiin-6-yl)-2-methoxyiminoacetic acid (syn isomer, 1.0 g.) were added to the solution, and stirred at the same temperature for 20 minutes to give an activated acid solution. On the other hand, trimethylsilylacetamide (4.6 g.) was added to a solution of 7-amino-3-(1H,-1,2,3-triazol-5-yl)thiomethyl-3-cephem-4-carboxylic acid (1.57 g.) in ethyl acetate (20 ml.), and stirred at 40° C. for 30 minutes. To the solution was added the activated acid solution all at once at −15° C. and stirred at the same temperature for an hour. Water (30 ml.) was added to the resultant solution, stirred for 5 minutes and then the ethyl acetate layer was separated.

The aqueous layer was extracted with ethyl acetate (20 ml.) and the extract was combined together with the ethyl acetate layer. Water (30 ml.) was added to the ethyl acetate solution and adjusted to pH 7.0 below 5° C. The aqueous layer was separated and adjusted to pH 2.7 with conc.hydrochloric acid. The precipitates were collected by filtration, washed with water and dried over phosphorus pentoxide to give 7-[2-(2,3-dihydro-1,4-oxathiin-6-yl)-2-methoxyiminoacetamido]-3-(1H-1,2,3-triazol-5-yl)thiomethyl-3-cephem-4-carboxylic acid (syn isomer, 1.2 g.)

I.R. $\nu_{max}{}^{Nujol}$: 3300, 3150, 1780, 1710, 1670 cm$^{-1}$.

N.M.R. $\delta$(DMSO-d$_6$, ppm): 3.17 (2H, m), 3.75 (2H, broad s), 3.83 (3H, s), 4.0 (2H, q, J=13 Hz), 4.33 (2H, m), 5.17 (1H, d, J=5 Hz), 5.67 (1H, dd, J=9 Hz, 5 Hz), 5.80 (1H, s), 7.99 (1H, s), 9.67 (1H, d, J=9 Hz).

EXAMPLE 22

2-(2,3-Dihydro-1,4-oxathiin-6-yl)-2-n-propoxyiminoacetic acid (syn isomer, 1.55 g.), dry N,N-dimethylformamide (0.56 ml.), dry ethyl acetate (2.1 ml.) and phosphoryl chloride (0.66 ml.) were treated in a conventional manner to give an activated acid solution. On the other hand, 7-amino-3-(1-methyl-1H-tetrazol-5-yl)thiomethyl-3-cephem-4-carboxylic acid (2 g.) and trimethylsilylacetamide (5.6 g.) were added to dry ethyl acetate (40 ml.) and stirred at 40° C. for an hour. To the solution was added the activated acid solution at −15° C. and stirred at −10° to −20° C. for 2 hours. Water (50 ml.) was added to the resultant solution and the ethyl acetate layer was separated. Water (30 ml.) was added to the ethyl acetate layer and adjusted to pH 7.5 with sodium bicarbonate. The aqueous layer was separated, washed with ethyl acetate and adjusted to pH 2.0 with 10% hydrochloric acid. The precipitates were collected by filtration, washed with water and dried over phosphorus pentoxide under reduced pressure to give 7-[2-(2,3-dihydro-1,4-oxathiin-6-yl)-2-n-propoxyiminoacetamido]-3-(1-methyl-1H-tetrazol-5-yl)thiomethyl-3-cephem-4-carboxylic acid (syn isomer, 2.75 g.).

I.R. $\nu_{max}{}^{Nujol}$: 3300, 1783, 1730, 1680 cm$^{-1}$.

N.M.R. $\delta$(DMSO-d$_6$, ppm): 0.86 (3H, t, J=7.0 Hz), 1.25–1.85 (2H, m), 3.08 (2H, m), 3.68 (2H, m), 3.95 (2H, t, J=6.2 Hz), 4.29 (4H, m), 5.09 (1H, d, J=5 Hz), 6.72 (1H, s), 6.72 (1H, dd, J=5.0 Hz, 8.0 Hz), 10.18 (1H, d, J=8.0 Hz).

EXAMPLE 23

2-(2,3-Dihydro-1,4-oxathiin-6-yl)-2-n-propoxyiminoacetic acid (syn isomer, 1.6 g.), dry N,N-dimethylformamide (0.56 ml.), dry ethyl acetate (22.3 ml.) and phosphoryl chloride (0.69 ml.) were treated in a similar manner to that of Example 14 to give an activated acid solution. On the other hand, 7-amino-3-(1H-1,2,3-triazol-5-yl)thiomethyl-3-cephem-4-carboxylic acid (2.0 g.) and trimethylsilylacetamide (5.9 g.) were added to dry ethyl acetate (40 ml.), and stirred at 40° C. for an hour. To the solution was added the activated acid solution at −15° C. and stirred at −10° to −20° C. for 50 minutes. Water (30 ml.) was added to the resultant solution, and the ethyl acetate layer was separated. Water (30 ml.) was added to the ethyl acetate solution and adjusted to pH 7.0 with sodium bicarbonate. The aqueous solution was separated, washed with ethyl acetate and adjusted to pH 2.7 with 10% hydrochloric acid. The precipitates were collected by filtration, washed with water and dried over phosphorus pentoxide under reduced pressure. The product was added to diethyl ether (100 ml.) and stirred. The precipitates were collected by filtration and washed with diethyl ether to give 7-[2-(2,3-dihydro-1,4-oxathiin-6-yl)-2-n-propoxyiminoacetamido]-3-(1H-1,2,3-triazol-5-yl)thiomethyl-3-cephem-4-carboxylic acid (syn isomer, 2.33 g.).

I.R. $\nu_{max}^{Nujol}$: 3300, 1780, 1730, 1660 cm$^{-1}$.

N.M.R. $\delta$(DMSO-d$_6$, ppm): 0.86 (3H, t, J=7.4 Hz), 1.60–1.80 (2H, m), 3.08 (2H, m), 3.67 (2H, broad s), 3.80–4.17 (2H, m), 5.13 (1H, d, J=5.5 Hz), 5.70 (1H, dd, J=5.5 Hz, 9.0 Hz), 7.99 (1H, s).

EXAMPLE 24

Phosphoryl chloride (1.214 g.), N,N-dimethylformamide (0.579 g.) and ethyl acetate (3 ml.) were treated in a conventional manner to prepare a Vilsmeier reagent. To the reagent was added 2-(2,3-dihydro-1,4-oxathiin-6-yl)-2-n-hexyloxyiminoacetic acid (syn isomer, 2.00 g.) at −10° C., and stirred at the same temperature for 20 minutes. On the other hand, trimethylsilylacetamide (6.93 g.) was added to a suspension of 7-amino-3-(1-methyl-1H-tetrazol-5-yl)thiomethyl-3-cephem-4-carboxylic acid (2.18 g.) in ethyl acetate (50 ml.), and stirred at 40° C. for an hour. To the solution was added the activated acid solution at −10° C. and stirred at the same temperature for an hour. Water (20 ml.) was added to the resultant solution and the organic layer was separated. The solution was washed with water (20 ml.) twice and dried. After concentrating the solution in vacuo, the residue was pulverized with diisopropyl ether (50 ml.). The precipitates were collected by filtration and dried to give 7-[2-(2,3-dihydro-1,4-oxathiin-6-yl)-2-n-hexyloxyiminoacetamido]-3-(1-methyl-1H-tetrazol-5-yl)thiomethyl-3-cephem-4-carboxylic acid (syn isomer, 3.4 g.).

I.R. $\nu_{max}^{Nujol}$: 3280, 1785, 1730, 1675 cm$^{-1}$.

N.M.R. $\delta$(DMSO-d$_6$, ppm): 1.00 (3H, t, J=8 Hz), 1.17–1.94 (8H, m), 3.10 (2H, m), 3.73 (2H, m), 3.98 (3H, s), 4.00–4.33 (4H, m), 5.13 (1H, d, J=5 Hz), 5.73 (2H, m), 9.58 (1H, d, J=8 Hz).

EXAMPLE 25

Phosphoryl chloride (1.214 g.), N,N-dimethylformamide (0.579 g.) and ethyl acetate (3 ml.) were treated in a conventional manner to give a Vilmeier reagent. To the solution were added ethyl acetate (7 ml.) and 2-(2,3-dihydro-1,4-oxathiin-6-yl)-2-n-hexyloxyiminoacetic acid (syn isomer, 2.18 g.) and treated in a similar manner to that of Example 24 to give an activated acid solution. The solution was added to a solution of 7-amino-3-(1,3,4-thiadiazol-2-yl)thiomethyl-3-cephem-4-carboxylic acid (2.18 g.) and trimethylsilylacetamide (6.93 g.) in ethyl acetate (50 ml.), and the mixture was treated in a similar manner to that of Example 24 to give 7-[2-(2,3-dihydro-1,4-oxathiin-6-yl)-2-n-hexyloxyiminoacetamido]-3-(1,3,4-thiadiazol-2-yl)thiomethyl-3-cephem-4-carboxylic acid (syn isomer, 3.00 g.)

I.R. $\nu_{max}^{Nujol}$: 3250, 1785, 1725, 1675 cm$^{-1}$.

N.M.R. $\delta$(DMSO-d$_6$, ppm): 1.00 (3H, t, J=8 Hz), 1.17–1.90 (8H, m), 3.08 (2H, m), 3.70 (2H, m), 3.90–4.67 (6H, m), 5.18 (1H, d, J=5 Hz), 5.71 (2H, m), 9.55 (1H, s), 9.55 (1H, d, J=8 Hz).

EXAMPLE 26

A solution of 7-amino-3-(1H-1,2,3-triazol-5-yl)thiomethyl-3-cephem-4-carboxylic acid (1.57 g.) and trimethylsilylacetamide (4.6 g.) in ethyl acetate (20 ml.) and a mixture of 2-(2,3-dihydro-1,4-dithiin-5-yl)-2-methoxyiminoacetic acid (syn isomer, 1.1 g.), N,N-dimethylformamide (0.44 g.) and phosphoryl chloride (0.92 g.) were treated in a similar manner to that of Example 21 to give 7-[2-(2,3-dihydro-1,4-dithiin-5-yl)-2-methoxyiminoacetamido]-3-(1H-1,2,3-triazol-5-yl)thiomethyl-3-cephem-4-carboxylic acid (syn isomer, 1.85 g.).

I.R. $\nu_{max}^{Nujol}$: 3300, 1780, 1720, 1680 cm$^{-1}$.

N.M.R. $\delta$(DMSO-d$_6$, ppm): 3.23 (4H, s), 3.70 (2H, broad s), 3.83 (3H, s), 4.03 (2H, q, J=13 Hz), 5.17 (1H, d, J=4 Hz), 5.70 (1H, dd, J=8 Hz, 4 Hz), 6.63 (1H, s), 7.97 (1H, s), 9.73 (1H, d, J=8 Hz).

EXAMPLE 27

A solution of 7-amino-3-(1-n-hexyl-1H-tetrazol-5-yl)thiomethyl-3-cephem-4-carboxylic acid (2.0 g.) and trimethylsilylacetamide (4.6 g.) in dry ethyl acetate (40.0 ml.), and a solution of 2-(2,3-dihydro-1,4-oxathin-6-yl)-2-n-hexyloxyiminoacetic acid (syn isomer, 1.5 g.), dry N,N-dimethylformamide (0.44 g.) and phosphoryl chloride (0.92 g.) in ethyl acetate (21.75 ml.) were treated in a similar manner to that of Example 22 to give 7-[2-(2,3-dihydro-1,4-oxathiin-6-yl)-2-n-hexyloxyiminoacetamido]-3-(1-n-hexyl-1H-tetrazol-5-yl)thiomethyl-3-cephem-4-carboxylic acid (syn isomer, 2.26 g.).

I.R. $\nu_{max}^{Nujol}$: 3300, 1790, 1730, 1680, 1630 cm$^{-1}$.

N.M.R. $\delta$(DMSO-d$_6$, ppm): 0.60–2.13 (22H, m), 3.11 (2H, m), 3.72 (2H, m), 3.88–4.60 (8H, m), 5.13 (1H, d, J=5.0 Hz), 5.73 (1H, s, 1H, dd, J=5.0 Hz, 8.0 Hz), 9.59 (1H, d, J=8.0 Hz).

EXAMPLE 28

A solution of 2-(2,3-dihydro-1,4-oxathiin-6-yl)-2-methoxyiminoacetic acid (syn isomer, 1.4 g.), dry N,N-dimethylformamide (0.59 ml.) and phosphoryl chloride (1.17 g.) in dry ethyl acetate (12.3 ml.), and a solution of 7-amino-2-methyl-3-cephem-4-carboxylic acid (1.35 g.) and trimethylsilylacetamide (5.75 g.) in ethyl acetate (40 ml.) were treated in a similar manner to that of Example 14 to give 7-[2-(2,3-dihydro-1,4-oxathiin-6-yl)-2-methoxyiminoacetamido]-2-methyl-3-cephem-4-carboxylic acid (syn isomer, 1.45 g.)

I.R. $\nu_{max}^{Nujol}$: 3160, 1765, 1660, 1635 cm$^{-1}$.

N.M.R. $\delta$(DMSO-d$_6$, ppm): 1.42 (3H, d, J=7.0 Hz), 3.07 (2H, m), 3.79 (3H, s), 4.27 (2H, m), 5.03 (1H, d, J=5.0 Hz), 5.72 (2H, m), 6.40 (1H, d, J=7.0 Hz), 9.63 (1H, d, J=8.0 Hz).

EXAMPLE 29

(1) Dry N,N-dimethylformamide (1.26 ml.), phosphoryl chloride (1.48 ml.), 2-(2,3-dihydro-1,4-oxathiin-6-yl)-2-n-propoxyiminoacetic acid (syn isomer, 3.48 g.) and dry ethyl acetate (5 ml.) were treated in a conventional manner to give an activated acid solution. On the other hand, a solution of 4-nitrobenzyl 7-amino-3-cephem-4-carboxylate (5.0 g.) trimethylsilylacetamide (12.6 g.) and bis(trimethylsilyl)acetamide (8.3 g.) in ethyl acetate (700 ml.) was stirred at 40° C. for an hour. The activated acid solution was added all at once to the solution at −30° C. and stirred at −10° to −30° C. for 2 hours. After adding water (50 ml.) to the resultant solution, the ethyl acetate layer was separated. The solution was washed with a saturated aqueous solution of sodium bicarbonate and a saturated aqueous solution of sodium chloride in turn, dried over magnesium sulfate and concentrated in vacuo. The residue was pulverized with diisopropyl ether, and the precipitates were collected by filtration and washed with diisopropyl ether to give 4-nitrobenzyl 7-[2-(2,3-dihydro-1,4-oxathiin-6-yl)-2-n-propoxyiminoacetamido]-3-cephem-4-carboxylate (syn isomer, 6.80 g.).

I.R. $\nu_{max}^{Nujol}$: 3250, 1780, 1730, 1660 cm$^{-1}$.

N.M.R. δ(DMSO-d$_6$, ppm): 0.79 (3H, t, J=7.0 Hz), 1.52 (2H, m), 3.00 (2H, m), 3.55 (2H, m), 3.89 (2H, t, J=6 Hz), 4.20 (2H, m), 5.06 (1H, d, J=4 Hz), 5.33 (2H, s), 5.62 (1H, s), 5.75 (1H, dd, J=4.0 Hz, 8.0 Hz), 6.58 (1H, m), 7.62 (2H, d, J=8 Hz), 8.15 (2H, d, J=8.0 Hz), 9.54 (1H, d, J=8.0 Hz).

(2) 4-Nitrobenzyl 7-[2-(2,3-dihydro-1,4-oxathiin-6-yl)-2-n-propoxyiminoacetamido]-3-cephem-4-carboxylate (syn isomer, 6.7 g.), tetrahydrofuran (200 ml.), methanol (67 ml.), acetic acid (2 ml.), water (6 ml.) and 10% palladium-carbon (3.3 g.) were treated in a similar manner to that of Example 18-(2) to give 7-[2-(2,3-dihydro-1,4-oxathiin-6-yl)-2-n-propoxyiminoacetamido]-3-cephem-4-carboxylic acid (syn isomer, 2.59 g.).

I.R. $\nu_{max}^{Nujol}$: 3300, 1790, 1776, 1660 cm$^{-1}$.

N.M.R. δ (DMSO-d$_6$, ppm): 0.87 (3H, t, J=7.6 Hz), 1.30–1.96 (2H, m), 3.10 (2H, m), 3.60 (2H, d, J=4.0 Hz), 4.00 (2H, t, J=6.4 Hz), 4.31 (2H, m), 5.10 (1H, d, J=5.0 Hz), 5.72 (1H, s), 5.79 (1H, dd, J=5 Hz, 8 Hz), 6.48 (1H, m), 9.58 (1H, d, J=8.0 Hz).

EXAMPLE 30

N,N-Dimethylformamide (0.579 g.), phosphoryl chloride (1.214 g.) and ethyl acetate (3 ml.) were treated in a conventional manner to give a Vilsmeier reagent and the reagent was added to ethyl acetate (7 ml.). To the solution was added 2-(2,3-dihydro-1,4-oxathiin-6-yl)-2-n-hexyloxyiminoacetic acid (syn isomer, 2.00 g.) under stirring to give an activated acid solution. On the other hand, 7-amino-3-cephem-4-carboxylic acid (1.46 g.), trimethylsilylacetamide (3.84 g.), bis(trimethylsilyl)acetamide (4.40 ml.) and ethyl acetate (24 ml.) were stirred to prepare a solution. To the solution was added all at once the activated acid solution at −10° C., and stirred at the same temperature for 1.5 hours. After adding water (30 ml.) and ethyl acetate (15 ml.) to the resultant solution, the solution was shaken sufficiently and the organic layer was separated. An aqueous solution of sodium bicarbonate (30 ml.) was added to the organic solution, shaken sufficiently and the aqueous layer was separated. The solution was adjusted to pH 2.0 with conc.hydrochloric acid and extracted with ethyl acetate (60 ml.). The extract was washed with water (20 ml.) twice, dried over magnesium sulfate and concentrated in vacuo. The residue was pulverized with diisopropyl ether (50 ml.) and the precipitates were collected by filtration to give 7-[2-(2,3-dihydro-1,4-oxathiin-6-yl)-2-n-hexyloxyiminoacetamido]-3-cephem-4-carboxylic acid (syn isomer, 2.40 g.).

I. R. $\nu_{max}^{Nujol}$: 3280, 1785, 1730, 1660 cm$^{-1}$.

N.M.R. δ (DMSO-d$_6$, ppm): 0.67–1.83 (11H, m), 3.07 (2H, m), 3.60 (2H, q, J=14 Hz), 3.99 (2H, t, J=6 Hz), 4.37 (2H, m), 5.06 (1H, d, J=5 Hz), 5.68 (1H, s), 5.74 (1H, dd, J=5 Hz, 8Hz), 6.46 (1H, t, J=5 Hz), 9.55 (1H, dd, J=8 Hz).

EXAMPLE 31

N,N-dimethylformamide (0.175 g.), phosphoryl chloride (0.367 g.) and ethyl acetate (0.5 ml.) were treated in a conventional manner to prepare a Vilsmeier reagent and the reagent was added to ethyl acetate (5 ml.). To the solution was added 2-(2,3-dihydro-1,4-oxathiin-6-yl)-2-allyloxyiminoacetic acid (syn isomer, 0.500 g.) at −15° C. and stirred at the same temperature for 20 minutes to give an activated acid solution. The solution was added all at once to a solution of 7-amino-3-cephem-4-carboxylic acid (0.524 g.), trimethylsilylacetamide (1.4 g.) and bis(trimethylsilyl)acetamide (1.5 ml.) in ethyl acetate (7.5 ml.) at −15° C. and stirred at the same temperature for 2 hours. Water (10 ml.) was added to the resultant solution, adjusted to pH 7.0 with an aqueous solution of sodium bicarbonate and the aqueous layer was separated. The aqueous solution was adjusted to pH 3 with 10% hydrochloric acid. The precipitates were collected by filtration and washed with water to give 7-[2-(2,3-dihydro-1,4-oxathiin-6-yl)-2-allyloxyiminoacetamido]-3-cephem-4-carboxylic acid (syn isomer, 0.73 g.).

I. R. $\nu_{max}^{Nujol}$: 3225, 1770, 1708, 1660 cm$^{-1}$.

N.M.R. δ (DMSO-d$_6$, ppm): 3.07 (2H, m), 3.55 (2H, d, J=4 Hz), 4.27 (2H, m), 4.53 (2H, m), 5.07–5.40 (3H, m), 5.67–6.27 (3H, m), 6.45 (1H, t, J=4 Hz), 9.60 (1H, d, J=8 Hz).

EXAMPLE 32

(1) A solution of 4-nitrobenzyl 7-amino-3-chloro-3-cephem-4-carboxylate hydrochloride (5.0 g.) and trimethylsilylacetamide (11.3 g.) in dry ethyl acetate (100 ml.) and a solution of 2-(2,3-dihydro-1,4-oxathiin-6-yl)-2-n-propoxyiminoacetic acid (syn isomer, 3.13 g.), dry N,N-dimethylformamide (1.13 ml.) and phosphoryl chloride (1.33 ml.) in ethyl acetate (54.4 ml.) were treated in a similar manner to that of Example 19-(1) to give 4-nitrobenzyl 7-[2-(2,3-dihydro-1,4-oxathiin-6-yl)-2-n-propoxyiminoacetamido]-3-chloro-3-cephem-4-carboxylate (syn isomer, 7.10 g).

I. R. $\nu_{max}^{Nujol}$: 1780, 1730, 1675, 1607 cm$^{-1}$.

N.M.R. δ (DMSO-d$_6$, ppm): 0.87 (3H, t, J=7.0 Hz), 1.30–1.90 (2H, m), 3.10 (2H, m), 3.98 (2H, t, J=6.4 Hz), 4.28 (2H, m), 5.32 (1H, d, J=5.0 Hz), 5.48 (2H, s), 5.73 (1H, s), 6.87 (1H, dd, J=5.0 Hz, 8.2 Hz), 7.74 (2H, d, J=9.0 Hz), 8.29 (2H, d, J=9.0 Hz).

(2) 4-Nitrobenzyl 7-[2-(2,3-dihydro-1,4-oxathiin-6-yl)-2-n-propoxyiminoacetamido]-3-chloro-3-cephem-4-carboxylate (syn isomer, 7.0 g.), acetic acid (2 ml.), water (10 ml.), 10% palladium-carbon (3.5 g.). tetrahydrofuran (100 ml.) and methanol (100 ml.) were treated in a similar manner to that of Example 19-(2). The obtained crystals were recrystallized from methylene chloride (20 ml.) to give 7-[2-(2,3-dihydro-1,4-oxathiin-6-yl)-2-n-propoxyiminoacetamido]-3-chloro-3-cephem-4-carboxylic acid (syn isomer, 2.31 g.).

I. R. $\nu_{max}^{Nujol}$: 3300, 1784, 1740, 1665 cm$^{-1}$.

N.M.R. δ (DMSO-d$_6$, ppm): 0.87 (3H, t, J=8.0 Hz), 1.61 (2H, m), 3.08 (2H, m), 3.83 (2H, q, J=16.8 Hz), 3.97 (2H, t, J=8.0 Hz), 4.28 (2H, m), 5.23 (1H, d, J=5.0 Hz), 5.68 (1H, s), 5.74 (1H, dd, J=5.0 Hz, 9.0 Hz), 9.64 (1H, d, J=9.0 Hz).

EXAMPLE 33

(1) A solution of 4-nitrobenzyl 7-amino-3-chloro-3-cephem-4-carboxylate hydrochloride (4.06 g.) and trimethylsilylacetamide (9.19 g.) in ethyl acetate (40 ml.) and a solution of 2-(2,3-dihydro-1,4-dithiin-5-yl)-2-methoxyiminoacetic acid (syn isomer, 2.2 g.), N,N-dimethylformamide (0.8 g.) and phosphoryl chloride (1.67 g.) in ethyl acetate (24 ml.) were treated in a similar manner to that of Example 19-(1) to give 4-nitrobenzyl 7-[2-(2,3-dihydro-1,4-dithiin-5-yl)-2-methoxyiminoacetamido]-3-chloro-3-cephem-4-carboxylate (syn isomer, 5.1 g.).

I. R. $\nu_{max}^{Nujol}$: 3280, 1790, 1740, 1680 cm$^{-1}$.

N.M.R. $\delta$ (DMSO-d$_6$, ppm): 3.20 (4H, s), 3.80 (3H, s), 3.93 (2H, AB-q, J=18 Hz), 5.30 (1H, d, J=5 Hz), 5.48 (2H, s), 5.87 (1H, dd, J=8 Hz, 5 Hz), 6.6 (1H, s), 7.73 (2H, d, J=9 Hz), 8.30 (2H, d, J=9 Hz), 9.63 (1H, d, J=8 Hz).

(2) 4-Nitrobenzyl 7-[2-(2,3-dihydro-1,4-dithiin-5-yl)-2-methoxyiminoacetamido]-3-chloro-3-cephem-4-carboxylate (syn isomer, 5.0 g.), tetrahydrofuran (50 ml.), methanol (30 ml.), 10% palladium-carbon (2 g.), water (7 ml.) and acetic acid (0.7 ml.) were treated in a similar manner to that of Example 19-(2) to give 7-[2-(2,3-dihydro-1,4-dithiin-5-yl)-2-methoxyiminoacetamido]-3-chloro-3-cephem-4-carboxylic acid (syn isomer, 1.6 g.).

I. R. $\nu_{max}^{Nujol}$: 3300, 1780, 1730, 1660 cm$^{-1}$.

N.M.R. $\delta$ (DMSO-d$_6$, ppm): 3.20 (4H, s), 3.81 (2H, AB-q, J=18 Hz), 3.80 (3H, s), 5.72 (1H, dd, J=8 Hz, 5 Hz), 6.55 (1H, s), 9.77 (1H, d, J=8 Hz).

What we claim is:

1. A compound of the formula:

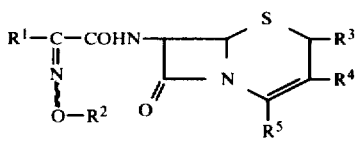

wherein R$^1$ is a group of the formula:

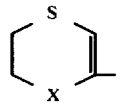

in which
X is sulfur, oxygen, imino or lower alkanoyl-substituted imino,
R$^2$ is hydrogen, lower alkyl or lower alkenyl,
R$^3$ is hydrogen or lower alkyl,
R$^4$ is hydrogen, halogen, lower alkyl, carbamoyloxymethyl or lower alkanoyloxymethyl, and
R$^5$ is carboxy or its ester, and a non-toxic, pharmaceutically acceptable salt thereof.

2. A compound according to claim 1, wherein R$^3$ is hydrogen.

3. A compound according to claim 2, wherein R$^4$ is hydrogen.

4. A compound according to claim 3, wherein R$^1$ is a group of the formula:

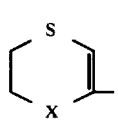

in which X is sulfur, oxygen or imino, and R$^5$ is carboxy.

5. A compound according to claim 4, wherein the compound is 7-[2-(2,3-dihydro-1,4-dithiin-5-yl)-2-methoxyiminoacetamido]-3-cephem-4-carboxylic acid.

6. A compound according to claim 4, wherein the compound is 7-[2-(2,3-dihydro-1,4-thiazin-5-yl)-2-hydroxyiminoacetamido]-3-cephem-4-carboxylic acid.

7. A compound according to claim 4, wherein the compound is 7-[2-(2,3-dihydro-1,4-oxathiin-6-yl)-2-methoxyiminoacetamido]-3-cephem-4-carboxylic acid.

8. A compound according to claim 4, wherein the compound is 7-[2-(2,3-dihydro-1,4-oxathiin-6-yl)-2-allyloxyiminoacetamido]-3-cephem-4-carboxylic acid.

9. A compound according to claim 2,
wherein R$^4$ is halogen.

10. A compound according to claim 9,
wherein R$^1$ is a group of the formula:

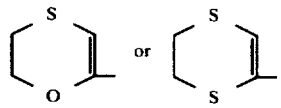

R$^2$ is lower alkyl, and
R$^5$ is carboxy.

11. A compound according to claim 10, wherein the compound is 7-[2-(2,3-dihydro-1,4-oxathiin-6-yl)-2-methoxyaminoacetamido]-3-chloro-3-cephem-4-carboxylic acid.

12. A compound according to claim 2,
wherein R$^4$ is lower alkyl.

13. The compound according to claim 12,
wherein R$^1$ is a group of the formula:

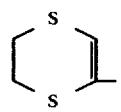

R$^2$ is lower alkyl, and
R$^5$ is carboxy.

14. A compound according to claim 13, wherein the compound is 7-[2-(2,3-dihydro-1,4-dithiin-5-yl)-2-methoxyiminoacetamido]-3-methyl-3-cephem-4-carboxylic acid.

15. A compound according to claim 2,
wherein R$^4$ is carbamoyloxymethyl or lower alkanoyloxymethyl.

16. A compound according to claim 15,
wherein R$^1$ is a group of the formula:

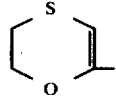

R$^2$ is lower alkyl,
R$^4$ is carbamoyloxymethyl or lower alkanoyloxymethyl, and
R$^5$ is carboxy.

17. A compound according to claim 16, wherein the compound is 7-[2-(2,3-dihydro-1,4-oxathiin-6-yl)-2-methoxyiminoacetamido]-3-carbamoyloxymethyl-3-cephem-4-carboxylic acid.

18. A compound according to claim 16, wherein the compound is 7-[2-(2,3-dihydro-1,4-oxathiin-6-yl)-2-methoxyiminoacetamido]cephalosporoanic acid.

19. A compound according to claim 1, wherein $R^3$ is lower alkyl, and $R^4$ is hydrogen.

20. A compound according to claim 19, wherein $R^1$ is a group of the formula:

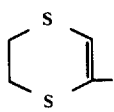

or

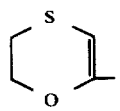

$R^2$ is lower alkyl, and $R^5$ is carboxy.

21. A compound according to claim 20, wherein the compound is 7-[2-(2,3-dihydro-1,4-dithiin-5-yl)-2-methoxyiminoacetamido]-2-methyl-3-cephem-4-carboxylic acid.

22. A compound according to claim 1, wherein X is sulfur, oxygen or imino, $R^5$ is carboxy.

23. A compound according to claim 1, wherein X is lower alkanoyl-substituted imino, and $R^5$ is carboxy.

24. A syn isomer of a compound according to any one of claims 1 through 18 and 19 through 23.

25. A compound according to claim 4, wherein the compound is 7-[2-(2,3-dihydro-1,4-oxathiin-6-yl)-2-n-propoxyiminoacetamido]-3-cephem-4-carboxylic acid.

26. A compound according to claim 4, wherein the compound is 7-[2-(2,3-dihydro-1,4-oxathiin-6-yl)-2-n-hexyloxyiminoacetamido]-3-cephem-4-carboxylic acid.

27. A compound according to claim 10, wherein the compound is 7-[2-(2,3-dihydro-1,4-oxathiin-6-yl)-2-n-propoxyiminoacetamido]-3-chloro-3-cephem-4-carboxylic acid.

28. A compound according to claim 2, wherein the compound is 7-[2-(2,3-dihydro-1,4-dithiin-5-yl)-2-methoxyiminoacetamido]-3-chloro-3-cephem-4-carboxylic acid.

29. A compound according to claim 2, wherein, the compound is 7-[2-(2,3-dihydro-1,4-oxathiin-6-yl)-2-methoxyiminoacetamido]-2-methyl-3-cephem-4-carboxylic acid.

30. A pharmaceutical composition which comprises an effective amount of a compound according to claim 1 as an active ingredient and pharmaceutically acceptable, nontoxic carrier(s).

* * * * *